(12) United States Patent
Benevolensky et al.

(10) Patent No.: US 7,910,327 B2
(45) Date of Patent: Mar. 22, 2011

(54) RECOMBINANT ALPHA-FETOPROTEIN AND METHOD OF PREPARING

(75) Inventors: Sergei Vladimirovich Benevolensky, Moscow (RU); Alexei Nikolaevich Marchenko, Moscow (RU); Dmitry Georgievich Kozlov, Moscow (RU); Sergei Sergeevich Zatsepin, Moscow (RU); Lyudmila Nikolaevna Shingarova, Moscow (RU); Igor Vyacheslavovich Dudich, Moskovskaya Obl. (RU); Lidiya Nikolaevna Semenkova, Moskovskaya Obl. (RU); Dmitry Igorevich Dudich, Moskovskaya Obl. (RU); Eduard Borisovich Tatulov, Moscow (RU); Elena Ivanovna Dudich, Moskovskaya Obl. (RU)

(73) Assignees: Elena Ivanovna Dudich, Moskovskaya obl. (RU); Eduard Borisovich Tatulov, Moscow (RU)

( * ) Notice: Subject to any disclaimer, the term of this patent is extended or adjusted under 35 U.S.C. 154(b) by 758 days.

(21) Appl. No.: 11/632,409

(22) PCT Filed: Jul. 7, 2005

(86) PCT No.: PCT/RU2005/000369
§ 371 (c)(1),
(2), (4) Date: Jan. 12, 2007

(87) PCT Pub. No.: WO2006/009492
PCT Pub. Date: Jan. 26, 2006

(65) Prior Publication Data
US 2009/0233849 A1 Sep. 17, 2009

(30) Foreign Application Priority Data
Jul. 14, 2004 (EA) ................................. 200400907

(51) Int. Cl.
C12P 21/02 (2006.01)
C12N 1/16 (2006.01)
C12N 1/19 (2006.01)
C12N 5/00 (2006.01)
C12N 15/12 (2006.01)
C12N 15/81 (2006.01)
C07K 14/435 (2006.01)

(52) U.S. Cl. ................. 435/69.1; 435/254.2; 435/320.1; 435/325; 530/350

(58) Field of Classification Search ........................ None
See application file for complete search history.

(56) References Cited

U.S. PATENT DOCUMENTS

| 5,139,936 A | 8/1992 | Botstein et al. |
| 5,206,153 A | 4/1993 | Tamaoki |
| 5,773,245 A | 6/1998 | Wittrup et al. |
| 5,965,528 A | 10/1999 | Murgita |
| 6,183,989 B1 | 2/2001 | Brandt et al. |
| 6,288,034 B1 | 9/2001 | Murgita |
| 6,331,611 B1 | 12/2001 | Murgita |
| 6,416,734 B1 | 7/2002 | Murgita |
| 6,627,440 B1 | 9/2003 | Murgita |

FOREIGN PATENT DOCUMENTS

| RU | 2142784 C1 | 12/1999 |
| RU | 2142785 C1 | 12/1999 |

OTHER PUBLICATIONS pUC18 plasmid DNA datasheet from GenScript, www.genscript.com; downloaded on Jan. 8, 2010.*
Bennett et al, α-Fetoprotein Derived form a Human Hepatoma Prevents Grwoth of Estrogen-dependent Human Breast Cancer Xenografts, Clinical Cancer Research, vol. 4, pp. 2877-2884, (Nov. 1998).
Morinaga et al, Primary Structures of Human α-Fetoprotein and its mRNA, Proc.Natl. Acad. Sci., vol. 80, pp. 4604-4608, (Aug. 1983).
Pucci et al, Human α-Fetoprotein Primary Structure: A Mass Spectrometric Study, Biochemistry, 30, pp. 5061-5066, (May 1991).
Semenkova et al, α-Fetoprotein Positively Regulates Cytochrome c-Mediated Caspase Activation and Apoptosome Complex Formation, Eur. J. Biochem. 270, pp. 4388-4399, (Sep. 2003).
Robinson et al, Reduction of BiP Levels Decreases Heterologous Protein Secretion in *Saccharomyces cerevisiae*, The Journal of Biological Chemistry, vol. 271, No. 17, pp. 10017-10022, (Apr. 1996).
Yamashita et al, Sugar Chains of Human Cord Serum α-Fetoprotein: Characteristics of N-Linked Sugar Chains of Glycoproteins Produced in Human Liver and Hepatocellular Carcinomas, Cancer Research, 53, pp. 2970-2975, (Jul. 1993).
Ritsu Yamamoto et al, Expression of Human α-fetoprotein in Yeast, Life Sciences, vol. 46(23), pp. 1679-1686, (1990).
Deutsch, Chemistry and Biology of α-Fetoprotien, Adv. Canc. Res. 56, pp. 253-312, (1991).
Mizejewski, Biological Role of α-Fetoprotein in Cancer: Prospects for Anticancer Therapy, Expert Rev. Anticancer Ther. 2(6):89-115, (2002).
Aussel and Masseyeff, Interaction of Retinoids and Bilirubin with the Binding of Arachidonic Acid to Human Alpha-Fetoprotein, Biochemical and Biophysical Research Communications, vol. 119, No. 3, pp. 1122-1128, (Mar. 30, 1984).
Deutsch H.F., The Uptake of Adriamycin-Arachidonic Acid Complexes by Human Tumor Cells in the Presence of α-Fetoprotein, Journal of Tumor Marker Oncology, vol. 9, No. 1, (1994).

(Continued)

*Primary Examiner* — Bridget E Bunner
(74) *Attorney, Agent, or Firm* — Howson & Howson LLP

(57) ABSTRACT

The invention relates to the microbiological and medical industry, genetic engineering, biotechnology. A *Saccharomyces cerevisiae* yeast strain was obtained on the basis of constructing a recombinant plasmid DNA comprising a structural gene of a human alpha-fetoprotein (AFP) under the control of a regulatory promoter, providing the synthesis and production of AFP in a secreted soluble form, this AFP having activity identical or similar to the activity of a human AFP. The obtained recombinant AFP may be used as an active substance for the preparation of therapeutic agents for use in oncology, immunotherapy, cosmetology and also for the diagnosis of cancer and embryonic pathologies.

6 Claims, 18 Drawing Sheets

OTHER PUBLICATIONS

Hard et al, O-Mannosylation of Recombinant Human Insulin-Like Growth Factor 1 (IGF-I) Produced in *Saccharomyces cerevisiae*, FEBS Letters, vol. 248, No. 1,2, pp. 111-114, (May 1989).

Uriel et al, AFP Receptors in Malignant Cells: an Overview, CRC Press, vol. 2:103-117, (1989).

Tsukada et al, Cytocidal Effect of Daunomycin-Unsaturated Fatty Acid Complexes on Rat Tumor Cell Lines, Journal of Tumor Marker Oncology, vol. 9, No. 1, (1994).

Bennett et al, Similarity Between Natural and Recombinant Human Alpha-Fetoprotein as Inhibitors of Estrogen-Dependent Breast Cancer Growth, Breast Cancer Research and Treatment, 45:169-179, (Sep. 1997).

Semenkova et al, Induction of Apoptosis in Human Hepatoma Cells by Alpha-Fetoprotein, Tumor Biol., 18:261-273, (Jan. 1997).

Dudich et al, Growth-Regulative Activity of Human Alpha-Fetoprotein for Different Types of Tumor and Normal Cells, Tumor Biol., 19:30-40, (1998).

Dudich et al, α-Fetoprotein Causes Apoptosis in Tumor Cells Via a Pathway Independent of CD95, TNFR1 and TNFR2 Through Activation of Caspase-3-like Proteases, Eur. Biochem., 266, pp. 750-761, (1999).

Nishi et al, Expression of Rat α-Fetoprotein cDNA in *Escherichia Coli* and in Yeast, J. Biochem, 104, pp. 968-972 (Dec. 1988).

Boismenu et al, Purification and Characterization of Human and Mouse Recombinant Alpha-Fetoproteins Expressed in *Escherichia Coli*, Protein Expression and Purification, 10, pp. 10-26, (Jun. 1997).

Shusta et al, Increasing the Secretory Capacity of *Saccharomyces cerevisiae* for Production of Single-Chain Antibody Fragments, Nature Biotechnology, vol. 16, pp. 773-777, (Aug. 1998).

Chung & Park, Simple Approach to Reducing Proteolysis During Secretary Production of Human Parathyroid Hormone in *Saccharomyces cerevisiae*, Biotechnology and Bioengineering, vol. 57, No. 2, (Jan. 20, 1998).

Kang et al, Proteolytic Stability of Recombinant Human Serum Albumin Secreted in the Yeast *Saccharomyces cerevisiae*, Appl. Microbiol Biotechnol, 53:575-582, (May 2000).

DeFreest, et al., Synthetic peptide derived from α-fetoprotein inhibits growth of human breast cancer: investigation of the pharmacophore and synthesis optimization, J. Peptide Res., 2004, pp. 409-414, vol. 63.

Feldman, et al., Antitumor Activity of α-Fetoprotein Conjugate with Doxorubicin in vitro and in vivo, Biochemistry (Moscow), 2000, pp. 1140-1145, vol. 65, No. 8.

Smith, et al., Heterologous Protein Secretion from Yeast, Science, Sep. 20, 1985, pp. 1219-1224, vol. 229.

Supplemental Search Report and Opinion mailed Mar. 17, 2008 in counterpart European Patent Application No. 05764041.9.

Examination Report dated Jul. 18, 2008 in counterpart European Patent Application No. 05764041.9.

Response and Claim Amendments dated Jan. 27, 2009 to Jul. 18, 2008 Examination Report in counterpart European Patent Application No. 05764041.9.

Examination Report dated Sep. 22, 2009 in counterpart European Patent Application No. 05764041.9.

Response dated Jan. 27, 2010 to Sep. 22, 2009 Examination Report in counterpart European Patent Application No. 05764041.9.

Examination Report dated Oct. 21, 2010 in counterpart European Patent Application No. 05764041.9.

\* cited by examiner

```
  1          11         21         31         41         51         61
aagcttagcctaaaaaaaacctctcttgaacttcagtaatacgcttaactgctcat
^HindIII
 61          71         81         91        101        111        121
tgctatattgaagtacggattagaagccgcgagcgggtgacagccctccgaaggaagac
                                      ^BsrBI
121         131        141        151        161        171        181
tctcctccgtgcgtcctcgtcctcaccggtcggttcctgaaacgcagatgtgcctcgcg 181         191        201        211        221        231        241
ccgcactgctccgaacaataaagattctacaatactagctttatgttatgaaggaggaa 241         251        261        271        281        291        301
aaattggcagtaacctggcccccacaaaccttcaaatgaacgaatcaaattaacaaccata 301         311        321        331        341        351        361
ggatgataatgcgattagttttttagccttattcctgggggtaattaatcagcggaagcgat
                                                       ^VspI
361         371        381        391        401        411        421
gattttgatctattaacagatatataaatgcaaaaactgcataaccacttaactaata
^Sau3A
421         431        441        451        461        471        481
cttcaaacattcgtttgtattcttattacttttcaaatgtaataaagtatcaacaaaa
```

FIG.2a

```
481         491         501         511         521         531         541
aattgttaatatacctctatacttaacgtcaaggagaaaactactaccatgagattcca                M  R  F  P    4
541         551         561         571         581         591         601                    ^BsaBI
 S  I  F  T  A  V  L  F  A  A  S  A  L  A  A  P  V  N  T                                       24
tctatcttcactgcagtttattcgcagcatcctcgcattcgcgtcctccagtcaacact
           ^PstI
601         611         621         631         641         651         661
 T  T  E  D  R  T  A  Q  I  P  A  E  A  V  I  G  Y  L  D  L                                    44
acaacagagagatgaaacggcacaaattccggctgaagctgtcatcggttactagattta
661         671         681         691         701         711         721
 E  G  D  F  D  V  A  V  L  P  F  S  N  S  T  N  G  L  L                                       64
gaagggggattcgatgttgctgttttgccatttccaacagcacaataacggttattg
721         731         741         751         761         771         781
 F  I  N  T  T  I  A  S  I  A  A  K  E  E  G  V  S  M  A  K                                    84
tttataaatactactattgccagcattgctgtgctaaagaagaaggggtatcatggctaaa
                                                              ^NcoI
781         791         801         811         821         831         841
 R  T  L  H  R  N  E  Y  G  I  A  S  I  L  D  S  Y  Q  C  T                                    104
aggacactgcatagaaatgaatatggaatagcttccatattggattcttaccaatgtact
                                                               ^PstI
```

FIG. 2b

```
841                  851                  861                 871                   881                   891                  901
 A   E    I    S    L    A    D    L    A    T    I    E    F    A    Q    F    V    Q    E    A                         124
gcagagataagtttagctgacctggctaccatattttgcccagttgttcaagaagcc
 901                  911                  921                 931                   941                   951                  961
 T    Y   K    E    V    S    K    M    V    K    D    A    L    T    A    I    E    K    P    T                         144
acttacaaggaagtaagcaaaatggtgaaagatgcattgactgcaattgagaaacccact
                                                             ^AvaIII.       ^MfeI.
 961                  971                  981                 991                  1001                  1011                 1021
 G   D   E    Q   S    S    G    C    L    E    N    Q    L    P    A    F    L    E    E    L                           164
ggagatgaacagtcttcaggtgtttagaaaaccagctaccagctgcctttctggaagaactt
1021                 1031                 1041                1051                  1061                  1071                 1081
 C   H   E    K    E    I    L    E    K    Y    G    H    S    D    C    C    S    Q    S    E                          184
tgccatgagaagaaaatttggagaagtacggacattcagactgctgcagccaaagtgaa
                                                                                          ^PstI.
1081                 1091                 1101                1111                  1121                  1131                 1141
 E   G    R   H    N    C    F    L    A    H    K    K    P    T    P    A    S    I    P    L                          204
gagggaagacataactgtttcttgcacacaaaagcccactccagcatccgatcccactt
                                                                                    ^ClaI.
                                                                                            ^Sau3A
1141                 1151                 1161                1171                  1181                  1191                 1201
 F   Q    V    P    E    P    V    T    S    C    E    A    Y    E    E    D    R    E    T    F                         224
ttccaagttccagaacctgtcacaagctgtgaagcatatgaagaagacagggagacattc
                                                                   ^NdeI.
                                                                                                                   ^BspHI FIG.2c
```

```
1201                1211       1221       1231       1241       1251       1261
     M  N  K  F  I  Y  E  I  A  R  R  H  P  F  L  Y  A  P  T  I                 244
     atgaacaaattcatttatgagatagcaagaaggcatccctgtatgcacctacaatt
      .         .         .         .         .         .         .
1261                1271       1281       1291       1301       1311       1321
     L  L  W  A  A  R  Y  D  K  I  I  P  S  C  C  K  A  E  N  A                 264
     cttctttgggctgctcgctatgacaaaataattccatcttgctgcaaagctgaaaatgca
      .         .         .         .         .         .         .
1321                1331       1341       1351       1361       1371       1381
     V  E  C  F  Q  T  K  A  A  T  V  K  E  L  R  E  S  S  L                    284
     gttgaatgcttccaaacaaaggcagcaacagttacaaagaattaagagaaagcagcttg
      .         .         .         .         .         .         .
1381                1391       1401       1411       1421       1431       1441
     L  N  Q  H  A  C  A  V  M  K  N  F  G  T  R  T  F  Q  A  I                 304
     ttaaatcaacatgcatgtgcagtaatgaaaaatttggacccgaactttccaagccata
                  ^AvaIII
      .         .         .         .         .         .         .
1441                1451       1461       1471       1481       1491       1501
     T  V  T  K  L  S  Q  K  F  T  K  V  N  F  T  E  I  Q  K  L                 324
     actgttactaaactgagtcagaagttaccaaagttaattttactgaaatccagaaacta
                                                             ^SpeI
      .         .         .         .         .         .         .
1501                1511       1521       1531       1541       1551       1561
     V  L  D  V  A  H  V  H  E  H  C  C  R  G  D  V  L  D  C  L                 344
     gtcctggatgtggcccatgtacatgagcactgttgcagggagatgtgctggattgtctg
                              ^Bsp1407I                         ^PstI
      .         .         .         .         .         .         .
1561                1571       1581       1591       1601       1611       1621
```

FIG.2d

```
     Q  D  G  E  K  I  M  S  Y  I  C  S  Q  Q  D  T  L  S  N  K            364
     caggatggggaaaaatcatgtcctacatatgttctcaacagacactctgtcaaacaaa
     1621       1631      1641      1651      1661      1671      1681
                                        ^NdeI
     I  T  E  C  C  K  L  T  L  E  R  G  Q  C  I  H  A  E                  384
     ataacagaatgctgctgcaaactgaccacgctggaacgtggtcaatgtataattcatgcagaa
     1681       1691      1701      1711      1721      1731      1741

N  D  E  K  P  E  G  L  S  P  N  L  N  R  F  L  G  D  R  D            404
     aatgatgaaaaacctgaaggtctatctccaaatctaaacaggttttaggagatagagat
     1741       1751      1761      1771      1781      1791      1801

F  N  Q  F  S  S  G  E  K  N  I  F  L  A  S  F  V  H  E  Y            424
     tttaaccaattttcttcaggggaaaaaatatctttttggcaagttttgttcatgaatat
     1801       1811      1821      1831      1841      1851      1861
                                                              ^BspHI
                                                                  ^SspI
     S  R  R  H  P  Q  L  A  V  S  V  I  L  R  V  A  K  G  Y  Q            444
     tcaagaagacatcctcagcttgctgtctcagtaattctaagagttgctaaaggataccag
     1861       1871      1881      1891      1901      1911      1921
         ^Bpu10I.
     E  L  L  E  K  C  F  Q  T  E  N  P  L  E  C  Q  D  K  G  E            464
     gagttattggagaagtgtttccagactgaaaaccctcttgaatgccaagataaaggagaa
     1921       1931      1941      1951      1961      1971      1981

E  L  Q  K  Y  I  Q  E  S  Q  A  L  A  K  R  S  C  G  L               484
     gaagaattacagaaatacatccaggagagccaagcattggcaaagcgaagctgcgggcctc
```

FIG.2e

```
1981            1991            2001            2011            2021            2031            2041  504
 F  Q  K  L  G   E  Y  L  Q  N  A  F  L  V  A  Y  T  K  K
ttccagaaactaggagaatattactacaaaatgcgtttctcgttgcttacacaaagaaa
                                 ^SspI 2041            2051            2061            2071            2081            2091            2101  524
 A  P  Q  L  T   S  S  E  L  M  A  I  T  R  K  M  A  A  T  A
gcccccagtgtgacctcgtcggagctgatggccatcaccagaaaaatggcagccacagca
       ^PvuII                           ^BsaBI
                                               ^BalI 2101            2111            2121            2131            2141            2151            2161  544
 A  T  C  C  Q   L  A  C  E  D  K  L  L  A  C  G  E  G  A  A  D
gccacttgttgccaactcgaggacaaactattggcctgtggcgaggagggctgac
                                                  ^BsrBI 2161            2171            2181            2191            2201            2211            2221  564
 I  I  G  H  L   C  I  R  H  E  M  T  P  V  N  P  G  V  G
attattatcggacacttatgtatcagacatgaaatgactccagtaaacccctggttggc
                                                      ^BalI 2221            2231            2241            2251            2261            2271            2281  584
 Q  C  C  T  S   Y  A  N  R  R  P  C  F  S  S  L  V  D
cagtgctgcacttcttcatatgccaacaggaggccatgcttcagcagcttggtgtggat
                   ^NdeI 2281            2291            2301            2311            2321            2331            2341  604
 E  T  Y  V  P   P  A  F  S  D  K  F  I  F  H  K  D  L  C
```

FIG.2f

```
gaaacatatgtccctcctgcattctctgatgacaagttcattttccataaggatctgtgc
     ^NdeI.                                          ^Sau3A
2341      2351      2361      2371      2381      2391      2401
 Q   A   Q   G   V   A   L   Q   T   M   K   Q   E   F   L   I   N   L   V   K   624
caagctcagggtgtagcgctgcaaacgatgaagcaagagagttctcattaaccttgtgaag
             ^Bpu10I ^Eco47III
2401      2411      2421      2431      2441      2451      2461
 Q   K   P   Q   I   T   E   E   Q   L   E   A   V   I   A   D   F   S   G   L   644
caaaagccacaataacagaggaacaacttgaggctgtcattgcagattctcaggcctg
                                                      ^StuI
2461      2471      2481      2491      2501      2511      2521
 L   E   K   C   C   Q   G   Q   E   Q   E   V   C   F   A   E   E   G   Q   K   664
ttggagaaatgctgctgccaaggccaaggaacaggaagtctgctttgctgaagagggacaaaaa
2521      2531      2541      2551
 L   I   S   K   T   R   A   A   L   G   V   *
ctgatttcaaaactcgtgctgctttggggagtttaa
```

```
  1   M  A  K  G  T  L  H  R  N  E  Y  G  I  A  S  I  L  D  S  Y   20
      atggc taaaggtacctt gcatagaaatgaatggtatgctgcttctatttttggattcttat
          ^NcoI     ^KpnI                                          61

21   Q  C  T  A  E  I  S  L  A  D  L  A  T  I  F  F  A  Q  F  V   40
      taccg atttccatggaacgtatctcttactgctgaacgattctatttttgctcaatttgtt
                                                              ^BsaBI 121

41   G  T  V  T  Y  K  E  V  S  K  M  V  K  D  A  L  T  A  I  E   60
      gttacatgtgacgactctaaagaaacgactaaccgatgaaaaatggagttaaacaa        181
      caagaagctacttataaagaagtttctaaaatggttaaagatgctttgactgctattgaa 61   K  P  T  G  D  E  Q  S  G  C  L  E  N  Q  L  P  A  F  L       80
      gttcttcttcgatgaacaactgagttcttaccaatttctacgaaactgacgataactt      241
      aaaccaactggtgatgaacaactctctggtttggaaaatcaattgccagctttttttg
                                                        ^MfeI        301

81   E  E  L  C  H  E  K  M  I  L  E  K  Y  G  H  S  D  C  C  S   100
      tttggttgaccactactgttagaagaacaaaccttttagttaacggtcgaaaaaac
      gaagaattgtgtcatgagaaaatgaaagaaataatggtcattctgattgtgttct         361

101   E  E  L  C  H  E  G  R  H  N  C  F  L  A  K  K  P  T  A  S   120
      cttcttaaacacagtactcttttctttaaagactactttatactgagtaagactaacaaga
      ^BspHI                                                         361

121   Q  S  E  E  G  R  H  N  C  F  L  A  K  K  P  T  A  S
      caatctgaagaaggtagacataattgtttttggctcataaaaaccaactccagctct
      gttagactccttctttccatctgtattaacaaaaaaacggagtattttttggttgaggtcgaaga
```

FIG.3b

```
361         371         381         391         401         411         421
    I  P  L  F  Q  V  P  E  P  V  T  S  C  E  A  Y  E  E  D  R              140
    attccattgttcaagttccagaaccagttacatcttgtgaagcatatgaagaagataga
                                                ^NdeI
421         431         441         451         461         471         481
    E  T  F  M  N  K  F  I  Y  E  I  A  R  R  E  P  F  L  Y  A              160
    taaggttaacaaagttcaaggtcttgtcaatgtcttgtagaacacttctctatgct
    gaaactttgaataatttatgaatatactactttaacgatctctctaggtaaaacatacga
491         501         511         521         531         541
    P  T  I  L  W  A  A  R  Y  D  K  I  P  S  C  C  K  A                    180
    caactattttgtgggctgctagatatgataaaattattccatctcttgtgtaaagct
    gttgataaaacacccgacgatctatactatttaataaggtagaacaaacatttcga
541         551         561         571         581         591         601
    E  N  A  V  E  C  F  Q  T  K  A  A  T  V  K  E  L  R  E                 200
    gaaaatgctgttgaatgttttcaaactaaagctgctactgtgtactaaagaattgagagaa
    ctttacgacaacttacaaagtttgattttgacgatgacatgattcttaactctctt
601         611         621         631         641         651         661
    S  S  L  N  Q  H  A  C  A  V  M  K  N  F  G  T  R  F                    220
    tcttctcttgaatcaacacgcatgcgctgttatgaaaaatttgggtactagaactttt
```

```
      agaagaaacaacttagtgttgtgcgtacgcgacaatacttttaaaaccatgatcttgaaaa
                 .         .         .         .         .         .
               661       671       681       691       701       711       721
                Q  A  I  T  V  T  K  L  S  Q  K  F  T  K  V  N  T  H  I       240
               caagctattactgttactaaattgtctcaaaaattcactaaagttaattttactgaatt
                                     ^SphI
               gttcgataatgacaatgatttaacagagttttaagattcaattaaaatgactttaa
                 .         .         .         .         .         .
               721       731       741       751       761       771       781
                Q  K  L  V  L  D  V  A  R  V  H  E  H  C  C  R  G  D  V  L    260
               caaaaattggtttggatgtttgtctcatgaacattgttgtagaggtgatgtttg
                                              ^BspHI
               gtttttaaccaaaacctacaacgagtacaagtacttgtaacaacatctccactacaaaac
                 .         .         .         .         .         .
               781       791       801       811       821       831       841
                D  C  L  Q  D  G  E  K  I  M  S  Y  I  C  S  Q  Q  D  T  L    280
               gattgttgcaagatggtgaaaaaattatgtcttatatttgtctcaacaagatacttg
               ctaacaacgttctaccactttttaatacagaatataaacaagagttgttctatgaaac
                 .         .         .         .         .         .
               841       851       861       871       881       891       901
                S  N  K  I  T  E  C  C  K  L  T  T  L  E  R  G  Q  C  I  I    300
               tctaataaaattactgaatgttgtaaattgactactttgaaagaggtcaatgcattatt
               agattatttaatgacttacaacattaactgatgaaacttctccagttacgtaataa
                                                                ^AvaIII
                 .         .         .         .         .         .
               901       911       921       931       941       951       961
                H  A  E  N  D  E  K  P  E  G  L  S  P  N  L  N  R  F  L  G    320
               catgctgaaaatgatgaaaaaccagaaggtttgtctccaaatttgaatagatttttgggt
               gtacgactttactactttttggtctttccaaacagaggtttaaacttatctaaaaaccca
                 .         .         .         .         .         .
```

```
 961        971        981        991       1001       1011       1021
  D  R  D  F  N  Q  F  S  G  E  K  N  I  F  L  A  S  F  V
gatagagatttaatcaatttctctggtgaaaaaatatttttggctccttgtt         340
ctatctctaaaattagttaaagagaccactttttataaaaaaccgaagaaacaa
         ^BsaBI                         ^SspI          ^BspHI 1021       1031       1041       1051       1061       1071       1081
  H  E  Y  S  R  R  H  P  Q  L  A  V  S  V  I  L  R  V  A  K
catgaatattctagaagagacatccacaattagctgtttctgtgttattgagagtgctaaa   360
gtacttataagatcttctctgtaggtgttaatcgacaaagacaataaactctcaacgattt
        ^SspI
            ^XbaI 1081       1091       1101       1111       1121       1131       1141
  G  Y  Q  E  L  L  E  K  C  F  Q  T  E  N  P  L  E  C  Q  D
ggttatcaagaattgttggaaaaatgtttccaaactgaaaatccattggaatgtcaagat   380
ccaatagttcttaacaaccttttacaaaggtttgactttaggtaaccttacagttcta
                                                            ^BglII
                                                            ^Sau3A 1141       1151       1161       1171       1181       1191       1201
  K  G  E  E  L  Q  K  Y  I  Q  E  S  Q  A  L  A  K  R  S
aaaggtgaagaattgcaaaaatatattcaagaatctcaagcattggctaaaagatct     400
tttccacttcttaacgttttatataagttcttagagttcgtaaccgattttctaga 1201       1211       1221       1231       1241       1251       1261
  C  G  L  F  Q  K  L  G  E  Y  Y  L  Q  N  A  F  L  V  A  Y
tgtggtttgtttcaaaaattgggtgaatattatttgcaaaatgctttttggttgcttat   420
acaccaaacaaagttttaacccacttataataaacgttttacgaaaaaccaacgaata
```

```
                                                                          1321
     1261    1271    1281    1291    1301    1311                          440
      T  K  A  P  Q  L  T  S  S  E  L  M  A  I  T  R  K  M  A
     actaaaaagctccacagctcaacttctctgaattgatggctattactagaaaatggct
     tgattttttcgaggtgtcgagttgaagagacttaactaccgataatgatcttttaccga
                 ^SspI 1381
     1321    1331    1341    1351    1361    1371                          460
      A  T  A  A  T  C  C  Q  L  S  E  D  K  L  L  A  C  G  E  G
     gctactgctgtacttgttgtcaattatcctgaagataaattgttggcttgtgtgaaggt
     cgatgacgacgatgaacaacagttaatagacttctatttaacaaccgaacaccacttcca 1441
     1381    1391    1401    1411    1421    1431                          480
      A  A  D  I  I  G  E  L  C  I  R  E  M  T  P  V  N  P
     gctgctgatatcattattggtgaattgtgtattagacatgaaatgactccagtaaatcca
     cgacgactatagtaataaccacttaacacataatctgtacttactgaggtcaattaggt
                   ^EcoRV 1501
     1441    1451    1461    1471    1481    1491                          500
      G  V  Q  C  C  T  S  Y  A  N  R  R  P  C  F  S  L
     ggtgttggtcaatgttgtacttcttatgctaatagaagaccatgtttttctcttttg
     ccacaaccagttacaacatgaagaatacgattatcttctggtacaaaagagaaaac 1561
     1501    1511    1521    1531    1541    1551                          520
      V  V  D  E  T  Y  V  P  P  A  F  S  D  D  K  F  I  F  K
     gttgttgatgaaacttatgttccaccagcttttctgatgataaattattttttcataa
     caacaactacttttgaatacaaggtggtcgaaaagactactatttaataaaaagtattt
```

FIG. 3e

```
1561      1571      1581      1591      1601      1611      1621
 D   L   C   Q   A   Q   G   V   A   L   Q   T   M   K   Q   E   F   L   I   N    540
gattgtgtcaagctcaaggtgttgtcaaactatgaaacaagaattcttgattaat
ctaaacacagttcgagttccacaacgaacgtttgatacttgttcttaagaactaatta
                                       ^EcoRI  ^VspI.

1621      1631      1641      1651      1661      1671      1681
 L   V   K   Q   K   P   Q   I   T   E   Q   L   E   A   V   I   A   D   F    560
:tggttaaacaaaaaccacaaattactgagaacaattagaagctgttattgctgatttt
aaccaattgtttttggtgttttaatgactcttgttaatcttcgacaataacgactaaaa 1681      1691      1701      1711      1721      1731      1741
 S   G   L   L   E   K   C   C   Q   G   Q   E   Q   E   V   C   F   A   E   E    580
cctggtttgttggaaaaatgtgtcaaggtcaagaacaagagtttgttttgctgaagaa
agaccaaacaaccacctttttacacagttccagttcttgttcttcaaacaaacgacttctt 1741      1751      1761      1771      1781      1791
 G   Q   K   L   I   S   K   T   R   A   A   L   G   V   &   L   E        597
ggtcaaaaattgatttctaaaactagagctgctttgggtgtttaactgagatat
ccagtttttaactaaagatttgatctcgacgaaacccacaaattgactctata
                                                  ^XhoI
```

FIG. 3f

RECOMBINANT ALPHA-FETOPROTEIN AND METHOD OF PREPARING

CROSS-REFERENCE TO RELATED APPLICATIONS

This is a national stage application under 35 USC 371 of PCT/RU2005/000369, filed Jul. 7, 2005.

FIELD OF THE INVENTION

The invention relates to the microbiological and medical industry, genetic engineering, biotechnology. A recombinant alpha-fetoprotein (AFP) according to the instant invention, retaining the activity of a human AFP, obtained from serum, is intended for use in oncology, immunotherapy, cosmetology.

BACKGROUND OF THE INVENTION

Alpha-fetoprotein (AFP) is the main component of embryonic blood serum of mammals, which is synthesized by embryonal liver and yolk sac during perinatal development. Immediately after birth, the level of AFP in the serum sharply decreases and its expression became undetectable in healthy adult individuals (Deutsch H. F., 1991, Adv. Canc. Res. 56, 253-312). The synthesis of AFP is renewed upon malignant development of liver tumors and germinogenic teratoblastomas and could be detectable to a lesser degree in the case of chemical and mechanical damage to the liver, accompanied by regeneration, for example, during acute viral hepatitis or cirrhosis (Mizejewsly G. J., 2002, Expert Rev. Anticancer. Ther. 2: 89-115).

Human AFP is a glycoprotein consisting of 590 amino acids and comprising about 4% of a carbohydrate component (Morinaga T., et al., 1983, Proc. Natl. Acad. Sci., U.S.A., 80, 4604-4608; Pucci P. et al., 1991, Biochemistry 30, 5061-5066). One of the main properties of AFP is the noncovalent sorption of different low-molecular chemical substances, such as polyunsaturated fatty acids, steroidal hormones, metals, retinoids, hydrophobic antibiotics and others (Aussel S. & Masseyeff R., 1994, Biochem. Biophys. Res. Commun. 119: 1122-1127; Deutsch H. F., 1994, J. Tumor Marker Oncol., 9: 11-14). In early stages of embryonic development, AFP replaces albumin as a transport vehicle for fatty acids and other low-molecular substances (Deutsch H. F., 1991, Adv. Canc. Res. 56, 253-312).

AFP molecule consists of three globular structural domains bounded by 15 interchain disulfide bonds, which significantly increases the complexity of the process of assembly of a tertiary structure of a protein (Morinaga T., et al., 1983, Proc. Natl. Acad. Sci. U.S.A., 80, 4604-4608; Pucci P., et al., 1991, Biochemistry 30, 5061-5066). Furthermore, all important structural element of an AFP molecule is the carbohydrate component, which provides correct reception and functioning of the molecule (Deutsch H. F., 1991, Adv. Canc. Res. 56, 253-312).

In addition to a polypeptide chain consisting of 590 amino acid residues, the structure of the molecule of a serum embryonic AFP or that one secreted by hepatocarcinoma cells includes one oligosaccharide group linked to asparagin according to the N-type glycosylation (Yamashita K. et al., 1993, Cancer Res. 53:2970-2975). The structure of an oligosaccharide AFP chain is heterogeneous and depends on different factors: the stage of development of hepatocarcinoma or the stage of development of the embryo. Oligosaccharides affect structural properties of an AFP molecule, could be included in the content of antigenic determinants and receptor-binding centers (Deutsch H. F., 1991, Adv. Canc. Res. 56, 253-312). As distinctive from serum AFP, recombinant AFP expressed in bacterial cells is not glycosylated, which is a characteristic distinction of the product characterized in the works of Murgita (U.S. Pat. Nos. 6,331,611; 6,627,440; 6,416,734) and, consequently, has structural and functional properties distinguishing it from a serum analog and also from the recombinant AFP expressed in yeast systems. It is known that during expression of heterologic proteins in yeasts, their glycosylation is carried out in respect to the same amino acid residues as in the serum analog, but the structure of the oligosaccharides themselves significantly differ in respect to makeup, length and branching of the chain, which also predetermines certain distinctions in the structural and functional properties of corresponding proteins (Hard K. et al., 1998, FEBS Lett. 248:111).

AFP may be selectively absorbed by cells expressing specific AFP receptors (AFPR), such as embryonic cells, stem cells, activated immune cells, cancer cells or cells transformed by certain types of retroviruses (Uriel J. et al., 1989, in Jizejewsky G. I., Jakobson H. I. (eds): Biological Properties of Alpha-Fetoprotein. Boca Raton, CRC Press, vol. 2:103-117). Normal mature cells lose the ability to absorb AFP and do not express specific AFPR. In view of this property of AFP, methods have been proposed for the therapeutic use of AFP for the purpose of targeting delivering of cytostatics and other substances, suppressing the growth of cancer cells, to a tumor (Deutsch H. F., 1994, J. Tumor Marker Oncol. 9: 11-14; Tsukada Y. et al., 1994, J. Tumor Marker Oncol. 9: 99-103).

AFP has a number of functional properties, which at present are being intensively studied. The classical concept of AFP as an analog of embryonic serum albumin, is at present supplemented by data concerning the capability of AFP to carry out the regulation of the growth, development and programmed death of cells (Mizejewslcy G. J., 2002, Expert Rev. Anticancer. Ther. 2: 89-115). In particular, it was shown that a recombinant AFP, similarly to a serum and cultural analog, is capable of suppressing the growth of estrogen-dependent tumoral and normal tissues (Bennett J. A. et al., 1997, Breast Cancer Res. Treat. 45, 169-179; Bennet J. A. et al., 1998, Clinical Cancer Research, 4, 2877-2884). Recently, it was established that the oncosuppressive activity of AFP is carried out in accordance with the mechanism of triggering apoptosis, which is characterized by typical morphological changes, the arrest of growth, by cytotoxicity and DNA fragmentation (Semenkova L. N., 1997, Tumor Biol. 18, 261-274; Dudich E. I., et al., 1998, Tumor Biol. 19, 30-40; Dudich E. I.; et al., 1999, Eur. J. Biochem. 266: 1-13; Semenkova L., et al., 2003, Eur.; J. Biochem. 70: 4388-4399).

Earlier studies showed the capability of AFP to regulate differentiation and activation of immune cells. In particular, AFP is capable to suppress immune cells activated with allo- or autoantigens and to inhibit various cytokine gene expression (Yamashita K., et al., 1993, Cancer Res. 53, 2970-2975; U.S. Pat. No. 5,965,528). On the other hand, AFP induces pronounced stimulation of the growth of immature bone marrow cells, stem cells and embryonic cells (Dudich E. I., et al., 1998, Tumor Biol. 19, 30-40; U.S. Pat. No. 6,627,440).

These properties of AFP, and also increased selectivity of absorption of AFP by cancer cells in vivo (Uriel J., et al., 1989, in Mizejewslcy G. I., Jakobson H. I., eds: Biological Properties of Alpha-Fetoprotein. Boca Raton, CRC Press. vol. 2:103-117), revealed the base for its use in medicine as a therapeutic preparation in the treatment of autoimmune (U.S. Pat. No. 5,965,528) and oncological diseases (U.S. Pat. No. 6,416,734; Mizejewslcy G. J., 2002, Expert Rev. Anticancer. Ther. 2: 89-115). Furthermore, traditionally AFP is used as an oncoembryonic marker for early diagnosis of oncological diseases and pathologies of embryonical development (Deutsch H. F., 1991, Adv. Canc. Res. 56, 253-312). However, the use of natural AFP as a drug is technologically impossible because of raw material deficiency.

Traditionally, a source for the obtainment of AFP is the blood serum of pregnant women, funic embryonal serum or ascitic fluid of cancer patients. Obviously, none of these sources are acceptable for the production of a protein substance for medical purpose because, in the first place, there is extremely limited access to the source of raw material and the content of AFP therein is low, and in the second place, there is the ever-growing risk of infection with viruses or prions.

Earlier data were published relating to the expression and purification of recombinant AFP (rAFP) in different microorganisms (Yamamoto R., et al., 1990, Life Sciences, 46:1679-1686; Nishi S., et al., 1988, J. Biochem. 104: 968-972; U.S. Pat. No. 5,206,153; U.S. Pat. No. 6,331,611). Thus, the intracellular production of human rAFP was carried out in *Saccharomyces cerevisiae* (Yamamoto R., et al., 1990, Life Sciences, 46:1679-1686; U.S. Pat. No. 5,206,153) and *Escherichia coli* (U.S. Pat. No. 6,331,611; Boismenu R., et al., 1997, Protein Expression and Purification. 10:10-26). It was shown that recombinant AFP, expressed in *Escherichia coli*, retains the immunoregulatory and oncosuppressive activity of the embryonic analog (Boismenu R., et al., 1997, Protein Expression and Purification. 10:10-26; Bennett J. A., et al., 1997, Breast Cancer Res. Treat. 45, 169-179). The main drawback of these expression systems is the incapability to secrete heterologic protein and the extremely low level of its production. Furthermore, the obtainment of the desired product from a biomass of recombinant strain-producers required that additional procedures of denaturation and renaturation be carried out, which resulted in a significant reduction of the yield of the product and, as a consequence, a substantial increase of its cost. Also, in the case of use of bacterial expression systems, the problem of contamination of the product with the lipopolysaccharides of the shell, which have known endotoxic activity, is also important.

The technical solution most similar to the instant invention is the strain-producer of human AFP that is described in the references (Yamamoto R., et al., 1990, Life Sciences, 46:1679-1686; U.S. Pat. No. 5,206,153). In these sources yeast strain-producer *Saccharomyces cerevisiae* with intracellular production of human AFP is disclosed, the amino acid sequence of which comprises an additional section corresponding to the signal peptide of rat AFP. This invention identifies the product of secretion of a yeast strain, which product has the properties of a mature human AFP and has the original sequence SEQ ID NO:4, which corresponds to the sequence of a mature human AFP. This specificity distinguishes the product described in the instant invention over the earlier disclosed (Yamamoto R., et al., 1990, Life Sciences, 46:1679-1686; U.S. Pat. No. 5,206,153). Furthermore, a drawback of this strain described in the cited references is the absence of mechanisms for intracellular assembly and secretion of AFP into a cultural liquid, which significantly raises the cost, makes the process of preparing a purified recombinant AFP in preparative amounts more complex and provides an extremely low level of production of AFP. Furthermore, the authors of the cited work (Yamamoto R., et al., 1990, Life Sciences, 46:1679-1686; U.S. Pat. No. 5,206,153) obtained a modified recombinant AFP, the sequence of which also comprises signal and linker peptide, which limits the possibility for its medical use because of modification of the structure of the protein, resulting in a change of the immunological specificity and, as a result thereof, in an increase of the risk of immunoreactive pathology with intravenous or subcutaneous administration.

In the case of heterological secretion production with yeast cells of proteins, for which the correct folding takes place with the formation of disulfide bonds (among them AFP), of importance is the level of production of yeast disulfidisomerase (Pdi) with cells of a producer (Shusta E. V., et al., 1998, Nat. Biotechnol. 16: 773-777). Furthermore, action synergic with this enzyme is provided by an increased amount of the shaperon-like yeast protein BiP (Robinson A. S., et al., 1996, J. Biol. Chem. 271: 10017-10022).

In spite of the fact that yeasts are traditionally considered to be organisms free of secreted proteinases (Chung B. H. & Park K. S., 1998, Biotechnol. Bioeng. 57:245-249), for a number of proteins, including—for HSA, their degradation in the course of culturing yeasts is shown, which is related to the presence of still unidentified proteinases associated with the cell (Chung B. H. & Park K. S., 1998, Biotechnol. Bioeng. 57:245-249; Kang H. A., et al., 2000, Appl. Microbiol. Biotechnol. 53: 575-582). All of the listed factors require that they be taken into account during the creation of a yeast producer of AFP, effectively secreted in a cultural liquid.

Taking the drawbacks of the methods existing at present for the preparation of a recombinant AFP into account, it becomes obvious that there is a need for further improvement of the technology of the systems for expression and secretion of recombinant AFP, in particular the development of new recombinant strains having the capability for higher expression of a heterological protein with the provision for intracellular assembly of a native tertiary structure and subsequent secretion of the desired product into a cultural liquid.

Thus, the requirement for the development of industrially applicable methods of preparing AFP, which in respect to its properties would be identical or similar to human serum AFP and thus would make it possible to use it in those fields where human serum AFP is traditionally used, objectively follows from the state of the art.

The achievement of the stated object is possible by the creation of a new strain of microorganisms, which could produce in a cultural medium a polypeptide identical or similar to human serum AFP in respect to its properties.

SUMMARY OF THE INVENTION

In order to prepare a recombinant AFP, the properties of which would be identical or similar to the properties of a human serum AFP, it was necessary to develop a strain-producer providing for synthesis and production of AFP in a secreted soluble form.

The strain-producer was obtained with the use of genetic engineering methods by transforming a parent strain with a plasmid, which comprised a DNA sequence encoding a protein having the activity of a mature human AFP.

A recombinant secreted AFP produced in a yeast system of expression has properties identical or similar to the properties of a mature human AFP, which are determined in an immunologic analysis and by its capability to suppress the growth of cells of B-cell lymphoma Raji and other human cellular lines sensitive to apoptogenic action in a culture in vitro. This provides for an identical mechanism of action of the obtained AFP and a mature human serum AFP, obtained by a traditional method and having an amino acid sequence presented as SEQ ID NO:4. The conditions for carrying out the method of preparing AFP according to the instant invention provides for the assembly of a polypeptide with minimum defects as compared with native human AFP.

The proximity of the properties of human recombinant AFP, produced in yeasts, and human serum AFP is provided by the inclusion of an expression cassette, comprising a DNA sequence encoding a mature human AFP, in the composition of the plasmid, in that the process of elation does not require the denaturation-renaturation step, and at the same time provides for glycosylation of the obtained polypeptide, and also folding of the molecule and formation of disulfide bonds. Recombinant human AFP produced in a secreted form in a yeast system of expression differs from the recombinant analog produced in a proeukaryotic system of expression in that it is glycosylated according to the N-type, while a recombinant bacterial AFP described in patents (Murgita R. A. U.S. Pat. Nos. 6,331,611; 6,627,440; 6,416,734) is not glycosylated. Human recombinant AFP produced in a secreted form in a yeast system of expression differs from the serum analog by the composition and structure of the oligosaccharide chain, which is determined by the yeast strain and composition of the sugars included in the nutrient medium.

In order to obtain a high yield of the secreted protein with the required activity from a host cell, several additional genes were added to the plasmid encoding the AFP gene, the additional genes providing a high level of gene transcription, folding of the proteins in the process of secretion and the correct formation of disulfide bonds.

As a result, a pKX plasmid was obtained having the capability of transforming cells for the expression and secretion of AFP.

A eukaryotic producer cell having the capability of secreting recombinant alpha-fetoprotein was obtained with the aid of the aforesaid plasmid.

In a preferable variant a recipient strain *Saccharomyces cerevisiae* YBS723 was used as the initial cell, this strain being transformed by pKX plasmid to obtain a strain-producer *Saccharomyces cerevisiae* YBS723/pKX, deposited in the Russian Collection of Industrial Microorganisms (VKPM) under No. Y-3115.

During the cultivation of a transformed strain, AFP is secreted into a medium from which it may be isolated in a pure form with the use of traditional biochemical methods.

An isolated AFP obtained from transformed cells is used in the content of a pharmaceutical composition inhibiting the growth of tumor cells, which comprises the obtained AFP and pharmaceutically acceptable carriers and excipients.

An isolated AFP is used in the makeup of a synergic composition, inhibiting the growth of tumor cells, which comprises the obtained AFP and chemotherapeutic preparations and pharmaceutically acceptable carriers and excipients.

With use of the isolated AFP, a pharmaceutical composition on the base thereof or comprising its synergic composition, a method for treating cancer or preventing its development has been developed, which presumes the administration to a patient of an effective amount of AFP, pharmaceutical composition or synergic composition.

Since the obtained AFP is similar in respect to properties to human serum AFP, the obtained AFP is used in the makeup of a synergic composition having an immunosuppressive and immunoregulating action, wherein the composition comprises AFP and cyclosporin C and pharmaceutically acceptable carriers and excipients.

A method for treating autoimmune diseases and correcting the immune status has been developed with use of the isolated AFP or aforesaid synergic composition, the method comprising administering to a patient an effective amount of an AFP or a synergic composition with cyclosporin C.

In view of the capability of AFP to stimulate growth of stem cells, the inventors have proposed a pharmaceutical composition stimulating the growth of stein cells, the composition comprising the obtained AFP and pharmaceutically acceptable carriers and excipients, and a synergic composition stimulating the growth of stem cells is also proposed, this composition comprising the obtained AFP and derivatives of vitamins A, E, D, antioxidants, steroid hormones, isoflavones of vegetative origin with pharmaceutically acceptable carriers and excipients.

A method for stimulating the growth of stem cells in vitro is proposed with use of the isolated AFP, the aforesaid pharmaceutical or synergistic composition, the method comprising acting on cells with an effective amount of AFP or corresponding compositions.

Furthermore, a method for stimulating the growth of stem cells in vivo is proposed, the method comprising administering to a patient an effective amount of AFP or the aforesaid pharmaceutical or synergistic composition.

A cosmetic composition for rejuvenating skin and preventing aging of the skin is proposed on the basis of functional activity of isolated AFP, the composition comprising the obtained AFP with carriers and excipients acceptable in cosmetology and, optionally, derivatives of vitamins A, E, D, antioxidants, steroid hormones, isoflavones of vegetative origin.

A method of using the obtained cosmetic composition for rejuvenating the skin and preventing aging of the skin is proposed within the frame of the instant invention, the method comprising applying the composition onto the skin of an individual.

BRIEF DESCRIPTION OF THE DRAWINGS

The following drawings illustrate the presented subject matters of the invention.

FIG. 2 shows FIGS. 2A-FIG. 2G show the structure of an expression cassette comprising a sequence encoding a human alpha-fetoprotein within the composition of a pKX plasmid. The promoter region of the MFα1 yeast gene is shown by dark print. The amino acid sequence of the human alpha-fetoprotein molecule is shown by capital letters.

FIG. 3A-FIG. 3F demonstrate the structure of a synthetic gene encoding AFP and consisting of the most often used yeast codons. The AFP amino acid sequences, which is identical to the amino acid sequence of serum human AFP, is singled out with dark print.

1. Marker proteins (94, 67, 43, 30, 20 kD).
2. rAFP after affinity chromatography on a column with anti-AFP-sepharose (0.3 µg).
3. rAFP after gel-chromatography on a column with Sephacryl S-200 (0.4 µg).
4. rAFP (0.1 µg).
5. rAFP after Sephacryl S-200 (0.6 µg).
6. rAFP after Sephacryl S-200 (0.5 µg).
7. Embryonic eAFP (0.4 µg).

Figure 5:
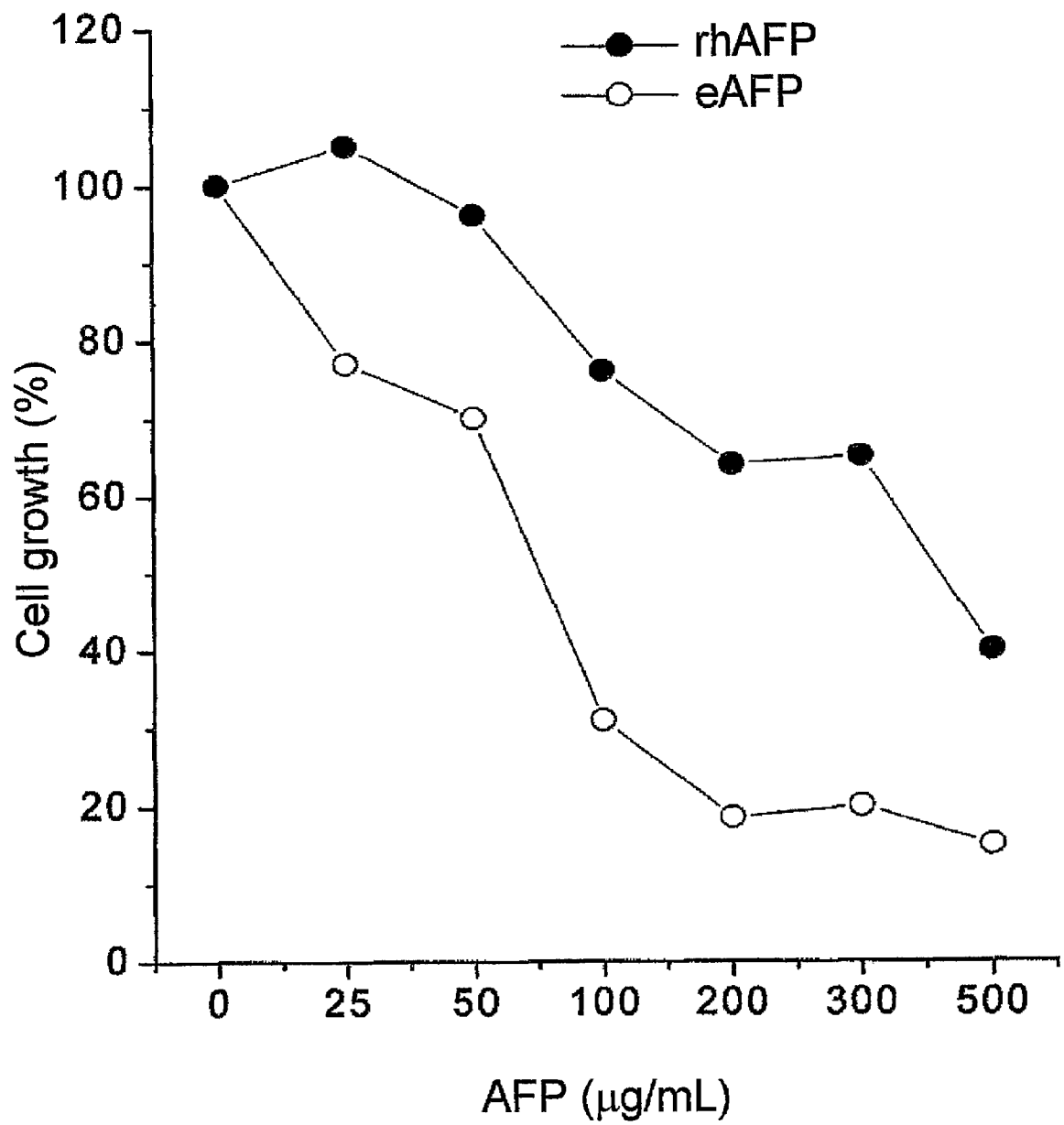

FIG. 5 shows a dose dependence of the proliferation of B-cellular Raji lymphoma cells on the AFP concentration for two different samples of purified AFP, which are obtained from embryonic serum eAFP and recombinant rAFP, that is expressed by yeast strain producer *Saccharomyces cerevisiae* YBS723/pKX. Proliferation of the cells was measured by [$H^3$]-thymidine incorporation and expressed in percentage of inhibition of growth in experimental cultures after 12-hour incubation with AFP in respect to a control without additives.

Figure 6:
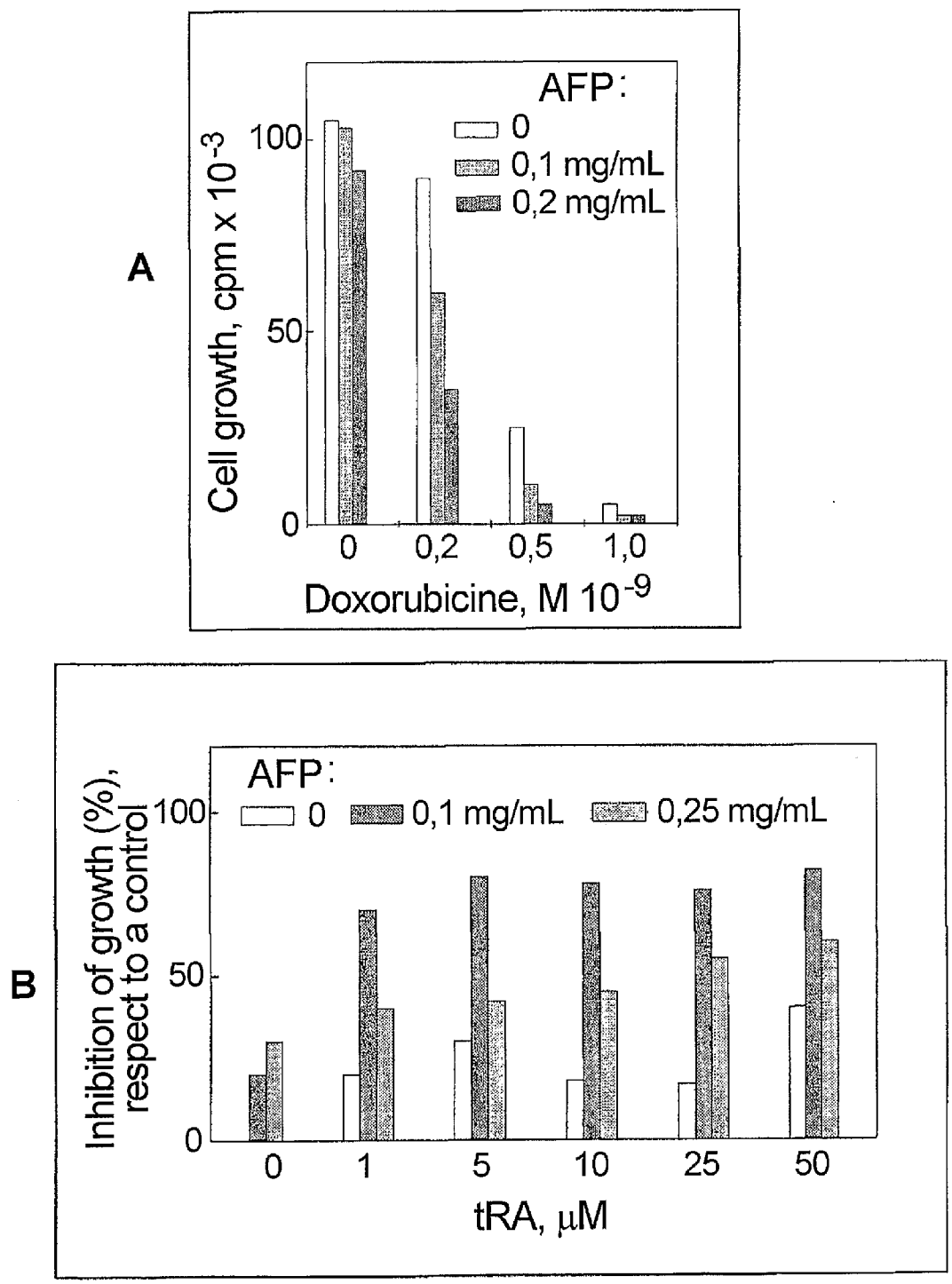

FIG. 6 demonstrates: (A) synergistic enhancement of oncosuppressive action of doxorubicine in respect to myeloblastoma U937 cells with the combined use with rAFP according to the instant invention;

(B) synergistic enhancement of the general oncosuppressive effect with combined use of rAFP according to the instant invention and retinoic acid (pro-vitamin A, acid). Proliferation of the cells was measured by [$H^3$]-thymidine incorporation and expressed in percentage of inhibition of growth in experimental cultures after 12-hour incubation with AFP in respect to a control without additives.

Figure 7:
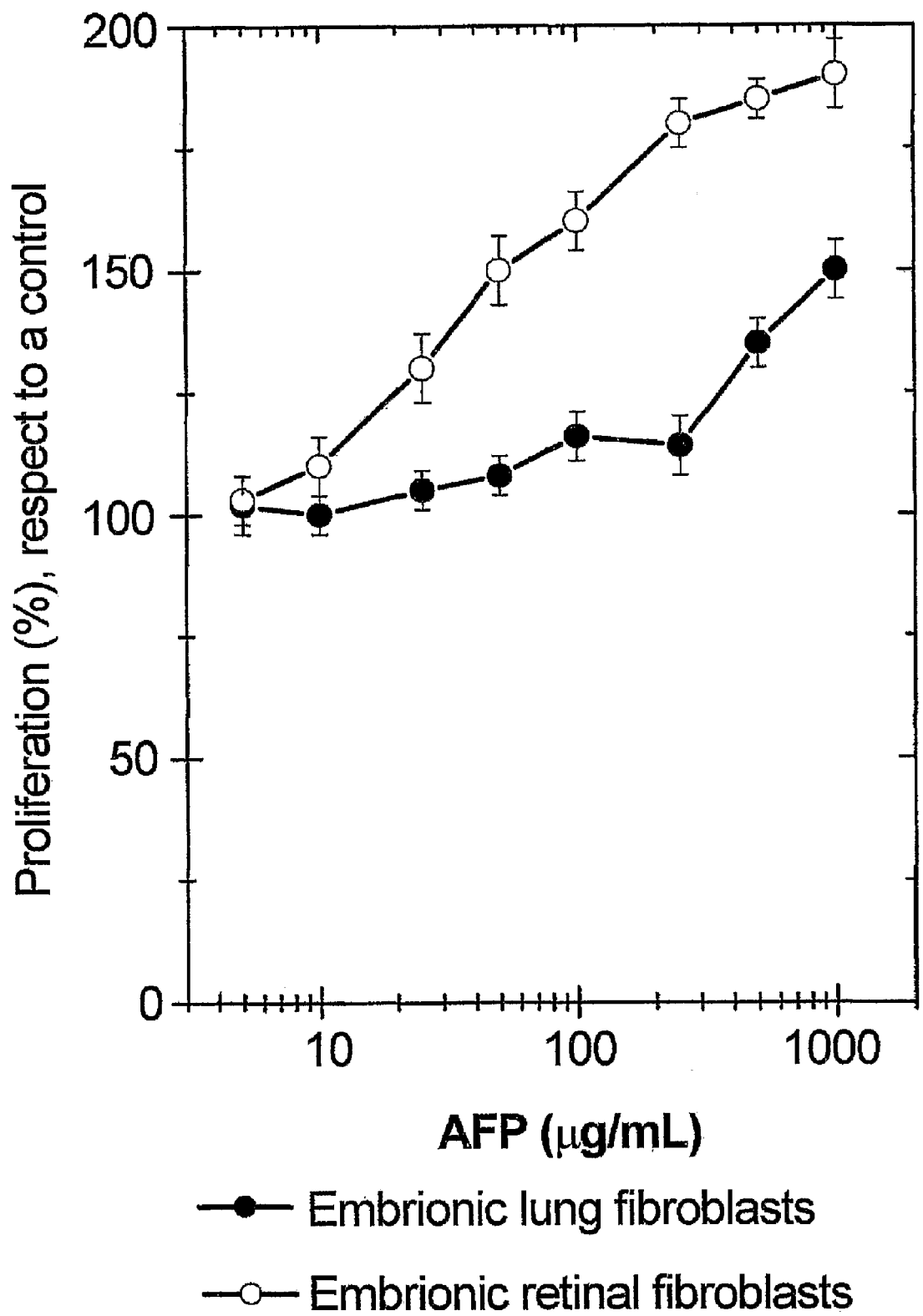

FIG. 7 shows the stimulating effect of rAFP according to the instant invention on the growth of stem embryonic cells obtained from a primary culture of cells of embryonic lung and retina. Proliferation of the cells was measured by a standard method of [$^3$]-thymidine incorporation during the last four hours of culture and expressed in percent of the stimulation of growth in test cultures in respect to a control without AFP.

The list of sequences comprises sequences SEQ ID NO:1 and SEQ ID NO: 4, which are respectively the nucleotide sequence of an expression cassette comprising the encoding sequence of a human alpha-fetoprotein in the composition of a pKX plasmid and the amino acid sequence of a mature human AFP.

The nucleotide sequence of an expression cassette comprises a promoter region of GAL1 yeast gene, a pre-pro region of secretion of MFα1 yeast gene, the encoding sequence of a human alpha-fetoprotein gene and a field of termination of transcription of a CYC1 yeast gene. This expression cassette is included in the composition of the pKX plasmid encoding the sequence of a mature human alpha-fetoprotein in a yeast strain-producer of a *Saccharomyces cerevisiae* YBS723/pKX system.

DETAILED DESCRIPTION OF THE INVENTION

In order to realize the instant invention, the main technical object was the creation of a strain of yeast-producer of AFP, capable of effectively secreting the desired protein into a cultural liquid. This object is solved by constructing a recombinant DNA pKX plasmid encoding the regulated synthesis of human AFP and the strain *Saccharomyces cerevisiae* YBS723/pKX providing the synthesis and production of AFP in a secreted dissolved form with a level of expression not less than 10 mg/l. The high level of synthesis of the desired protein in secreted dissolved form is provided in that the pKX plasmid comprises a promoter of the GAL1 gene with simultaneous amplification of the KAR2 gene (Robinson A. S., et al., 1996, J. Biol. Chem. 271:10017-10022), encoding a chaperon heavy chain binding protein BiP. In the genome of the strain of the recipient, there is amplification of the PD11 gene (Robinson A. S., et al., 1996, J. Biol. Chem. 271:10017-10022), encoding a disulfidisomerase enzyme, which participates in the formation of disulfide bonds during the secretory process of the proteins.

The recombinant plasmid DNA comprises a human AFP gene under the control of a GAL1 promoter gene, providing a high level of transcription of the gene, and a KAR2 gene, encoding a chaperon heavy chain binding protein BiP, participating in folding proteins during the secretory process for the proteins, and providing a high level of production of the desired protein into the cultural liquid. Furthermore, in order to provide the correct formation of disulfide bonds and the formation of a native tertiary structure of the protein, a PS11 gene encoding disulfideisomerase is used.

A recombinant pKX plasmid DNA (FIG. 1), encoding a human AFP gene, is characterized by the following features:
it is an expression plasmid for the effective secretion of human AFP;
it has a size of 13301 bp;
it comprises a fragment encoding the amino acid sequence of a mature human alpha-fetoprotein SEQ ID NO: 4;
it comprises a fragment of the bacterial plasmid pUC18; a region of initiation of a 2-μm yeast plasmid; a selective yeast marker PGK1; a KAR2 yeast gene encoding a chaperon heavy chain binding protein BiP; a PD11 gene encoding a disulfidisomerase enzyme; an expression cassette with an AFP genome;
in the structure of the expression cassette presented by the nucleotide sequence SEQ ID NO:1 is included: a promoter region of GAL1 yeast gene; a pre-pro region of secretion of MFα1 yeast gene; a region encoding a mature human AFP; a field of termination of transcription of a CYC1 yeast gene. When this plasmid is introduced into a cell, a high level of transcription of the AFP gene is achieved due to the use of a highly effective GAL1 promoter. The introduction of a pre-pro region of secretion of MFα1 provides for the correct secretory processing of AFP accompanied by the effective secretion of the protein with the expected amino acid sequence SEQ ID NO:4, if the encoding region will correspond to the DNA sequence encoding a mature human AFP in a cultural liquid;
a significant distinction of the proposed plasmid construction is that an afp gene is under the control of a highly effective GAL1 promoter, and in order to provide the correct formation of disulfide bonds and the formation of a native tertiary structure of the protein, PD11 and KAR2 genes are used.

Any eukaryotic cell susceptible to such a transformation with the indicated plasmid may be transformed with the aid of the created plasmid. The selection of the cell is not critical since the methods and steps of transformation are well-known to those skilled in the art. However, depending on the type of cell and the conditions for culturing the obtained transformant, the level of expression of AFP may vary, but the fact of expression of the required peptide will take place under condition of successful transformation of the parent cell.

A recipient strain YBS723 of the genotype pgk1/pgk1 is used to obtain the strain *Saccharomyces cerevisiae* YBS723/pKX. The homozygosis of pgk1/pgk1 makes this strain incapable of growth in all mediums containing any single source of carbon within the norm digestible by yeasts *S. cerevisiae*. The homozygosis of ga180::PD11/ga180: PD11 results in a change of regulation of the promoter of the GAL1 gene with simultaneous amplification in the genome of the PD11 gene encoding the disulfidisomerase enzyme and participating in the formation of disulfide bonds during the secretory process of the proteins.

The YBS723 strain is transformed by the pKX plasmid according to the method (Ito H., et al., 1983, J. Bacteriol. 153:163-168). Transformants were selected according to the capability to grow on a full-value yeast medium (bactopeptone—20 g/l, yeast extract—10 g/l, bactoagar—20 g/l) comprising 2% glucose as a source of carbon. One of such clones is designated as YBS723/pKX.

The obtained diploid yeast strain *Saccharomyces cerevisiae* YBS723/pKX is characterized by the following features:

Genetic features: Genotype pgk1/pgk1 ga180::PD11/ga180::PD11;

Morphological features: Vegetative cells of a 48-hour culture grown on a solid nutrient medium with 2% glucose as the only source of carbon have an oval form, cell size of 3.6×7.1 µm, the protoplasma is homogenous, reproduction is by gemmation. When growing on a solid medium comprising a yeast extract and peptone (YEP) at 30° C. after 72 hours of growth, the columns have the following appearance:

1) on a YEP medium with glucose—a white color column with a smooth edge, shining surface, cone-shaped profile, cream-like consistency;

2) on a YEP medium with starch—a white color column with a patterned edge, dull surface, lens-like profile and grain consistency;

3) on a YEP medium with molasses—a white color column with a dull wrinkled surface, patterned edge, convex profile and cream-like consistency.

Growth in a liquid medium—on a YEP medium with starch at 32° C. during the first 24 hours of culturing—a cloudy liquid, white residue, does not cake, does not form parietal films.

Physicochemical features: Facultative anaerobe. Temperature of growth—23-33° C. (optimum—31° C.). pH of culturing—3.8-6.7 (optimum—5.0). Highest level of secretion of AFP is observed at pH 6.8-7.0.

Assimilation of carbon sources: ferments glucose, galactose, fructose, maltose, saccharose, dextrine, starch.

Assimilation of nitrogen sources: assimilates amino acids, urea, ammonium sulphate, ammonium nitrate.

Distinctive specificities: in the case of culturing on a rich medium with starch (2%), zones of fading starch surrounded by a dark rim after incubation of dish at +4° C. for 24 h.

Pathogenicity: the strain *Saccharomyces cerevisiae* YBS723/pKX is not pathogenic.

Method of storage: The strain is stored on an agarized rich medium with glucose for 3 months at +4° C.

The obtained strain *Saccharomyces cerevisiae* YBS723/pKX—producer of AFP in a secreted form is deposited in the Russian Collection of Industrial Microorganisms (VKPM) under No. Y-3115.

The cell strain producer of recombinant AFP proposed by the Applicants has a number of advantages over already existing prototypes:

production of the desired product is carried out in a secreted form into a cultural liquid;

the amino acid sequence of the final product corresponds to the sequence of a mature human AFP—SEQ ID NO: 4;

similar to the serum embryonal analog, rAFP, produced by the strain producer *Saccharomyces cerevisiae* YBS723/pKX, is glycosylated;

the yield of the desired product is significantly increased due to an increase of expression of the gene encoding the disulfidisomerase enzyme PD11 providing for the formation of disulfide bonds and the KAR2 gene encoding shaperon heavy chain binding protein BiP providing for correct assembly of the protein and secretion of the desired product into the cultural medium.

It is completely obvious that the sequence encoding the DNA may comprise replacements related to degeneration of the genetic code, and also some replacements, insertions, deletions, which as a whole do not result in the obtainment of inactive forms of the fetoprotein. Possible variations are known to those skilled in the art. The obtained polypeptide may also include within the frame of the amino acid sequence conservative amino acid replacements presuming the replacement of one amino acid with another having similar properties. However, within the limits of the claimed features of the instant invention there are only those polypeptides which have primary, secondary and tertiary structure, that does not disturb the required activity of the obtained polypeptide, in particular—to have properties identical or similar to the properties of a mature human AFP, determined in an immunological analysis and in accordance with its capability to suppress the growth of cells of a B-cellular lymphoma Raji in a culture in vitro.

The indexes of functional activity, at which it is regarded that the obtained polypeptide will have the properties of a mature human serum AFP are determined according to the immunological reaction and according to its capability of inhibiting in vitro the growth of cells of the B-cellular lymphoma Raji at a level not less than 10% of the activity of a mature human serumal AFP cells of the B-cellular lymphoma Raji at a level not less than 10% of the activity of a mature human serum AFP.

In the case of practical use of the obtained polypeptide within the makeup of a composition, traditional additional components are used, such as excipients, diluents, preservatives, buffer solutions, physiological solution, a 0.9% solution of sodium chloride, technological additives used during the production of drug forms, etc. Compositions may be fluid (solutions, suspensions, creams, emulsions, etc.), solid (lyophilizated powder, reconstituted prior to use, an adsorbed preparation on a carrier, etc.), serving for parenteral, oral, intravenous, intramuscular, etc. administration or for external use. Wherein, the compositions for external use may comprise additives promoting the absorption and diffusion of the active substance in tissue.

The synergic compositions of the instant invention provide for the presence in the composition of another active substance, wherein in the case where two active substances are present at the same time, one of which is the AFP according to the instant invention, the effect of their action is reliably higher than in the case where each substance is used separately.

It is quite obvious that synergic compositions are one of the preferable variants of embodiment of the invention, since to one skilled in the art the variant of administering each active component separately is obvious. For example, in the case of anticancer therapy, each preparation of an active component may be administered separately and together simultaneously, with separation by time or by different manners of administration. The concrete selection depends on the state of the patient, the seriousness of the illness, prior treatment, etc.

The selection of the therapeutic dosages for treatment may be any dose in a wide range from 0.001-10 mg/kg of a patient's weight, with the proviso that the required therapeutic effect is obtained. It corresponds to the traditional dosages of human AFP, since the obtained AFP will have properties that are similar or close in respect to activity. The limiting dosages of AFP according to the invention correspond to the dosages of human AFP, since they have a similar amino acid sequence, which is not recognized by a normal immune system of a human as "foreign."

The instant invention is illustrated by the following examples, which are not of a restrictive character, but are intended to demonstrate embodiment of the invention and realization of the best variant of the embodiment.

Example 1

Isolation of Sum RNA and Construction of Intermediate Recombinant Plasmid DNA pTrcafp The total mRNA was isolated from the cellular line of human hepatoma HepG2 with the aid of Trizol Reagent (Gibco BRL, USA) in accordance with a method of the producer. The cDNA was obtained using First Strand cDNA Synthesis Kit (MBI Fermentas) in the presence of primers oligo (dT)$_{18}$ or GAAGTAATTTAAACTCCCAAAGC [SEQ ID NO: 5] (3R), complementary to the 3'-end of the gene afp. Amplification of the obtained matrix for subsequent cloning was carried out in the presence of primers:

```
                                      [SEQ ID NO: 6]
CTTCAATCGATATGACACTGCATAGAAATG (Cla)

[SEQ ID NO: 7]
CTTCCAAGCTTAAACTCCCAAAGCAG (Hind),
``` the first of which corresponds to the 5'-sequence of mature protein gene (singled out by dark print) and comprises the recognition site for restrictase Cla I, while the second is complementary to the 3'-end section of the gene (singled out by dark print) and comprises a recognition site for Hind III. Amplification of the gene was carried out in a volume of 100 µl. The reaction mixture comprised 10 ng of cDNA, 30 µM of each of primers (1) and (2), a mixture of dNTP (0.2 mM of each), 10 mM of Tris-HCl, pH 8.8, 10 mM of KCl, 2.5 mM of MgSO$_4$, 2.5 unit Pfu DNA-polymerases (Stratagene firm) and 1 unit Taq DNA-polymerase (Fernentas firm). There were 25 cycles carried out according to the scheme: 95° C./40 sec, 39° C./40 sec, 72° C./1 min. The products of the reaction were analyzed by electroforesis in a 1% agarous gel; strips of a length of about 1790 bp were cut, DNA was extracted from the gel, treated with restrictases ClaI and HindIII and cloned into the plasmid pTrcTEGF, earlier obtained on the base of the vector pTrc99A (Amann E., et al., 1988, *Gene*, 69, 301-315), and treated with those same restrictases. As a result the plasmid pTrcafp was obtained; its structure was confirmed by restrictase analysis, using restrictases Cla I and Hind III, in respect to which cloning was carried out, and also Spe I, Mun I, Sec I and Sty I, the recognition sites of which are inside the AFP gene, and by determination of the nucleotide sequence of the DNA section cloned with the aid of PCR. Sequencing was carried out according to the method and with use of the Cycle Reader™ DNA Sequencing Kit (Fermentas, Lithuania).

Example 2

Preparation of Synthetic cDNA, Encoding a Human AFP Gene

In order to obtain a synthesized AFP gene, 36 oligonucleotides having a length of 62-68 b were chemically synthesized. On the basis of these oligonucleotides six double-chain fragments were obtained by the method of polymerase chain reaction, each of which was cloned to a vector pUC18. The primary structure of all the cloned fragments was confirmed by sequencing. Fragments with the correct nucleotide structure were then sequentially collected into a desired gene by the method of restriction/ligation in the form of a fragment of the plasmid pUC18. In a similar manner a cDNA was obtained for expression of modified forms of AFP, comprising deletion, mutation or added amino acid residues.

Example 3

Construction of a Recombinant Plasmid DNA pKX

The Plasmid pTrcafp was Used as a Matrix for PCR in the Presence of Primers:

```
                                      [SEQ ID NO: 8]
CAACCCTCGAGTTAAACTCCCAAAGC

[SEQ ID NO: 9]
CCAACCCATGGCTAAGAGAACACTGCATAGAAA-TG.
```

Figure 1:
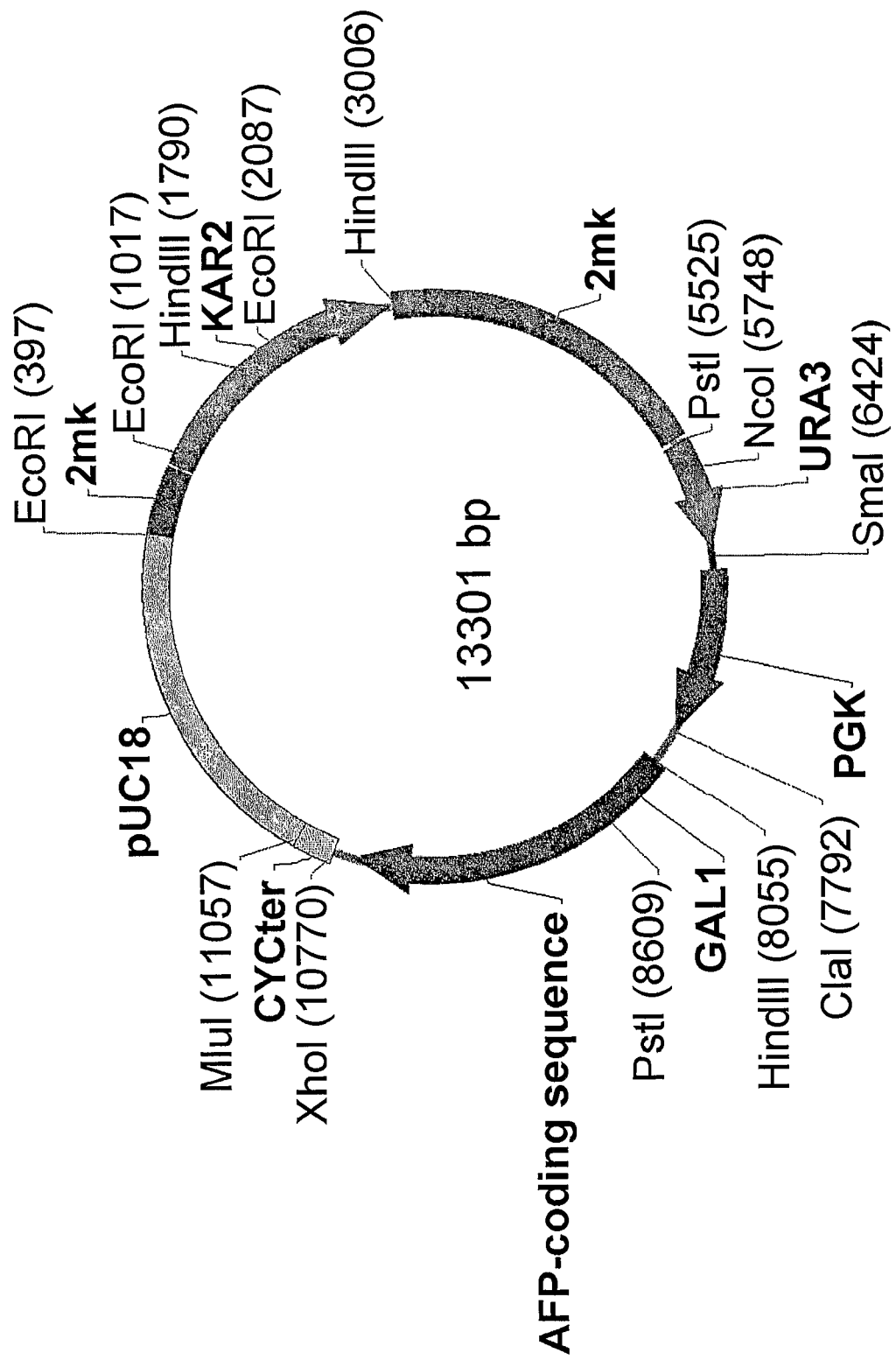
FIG. 1 shows the structure of a pKX plasmid encoding the sequence of a mature human alpha-fetoprotein, comprising an expression cassette with a human alpha-protein gene; a fragment of a bacterial plasmid pUC18; a region of initiation of replication of a 2-µm yeast plasmid; a selective PGK1 yeast marker, a PD11 gene encoding an disulfidisomerase enzyme and a KAR2 gene providing correct assembly of the protein and secretion of the desired product into a culture medium.

Restriction sites NcoI and XhoI (underlined) are set in the sequence of primers. The DNA fragment obtained as a result of amplification after treatment with endonucleases of restriction NcoI/XhoI were cloned onto vector pUC18/GAL1-pp, comprising a promoter GAL1 and pre-pro region of secretion MFα1. As a result the plasmid pUC18/GAL1-pp/afp was obtained. In order exclude possible errors of PCR the NcoI/XhoI fragment of the plasmid was sequenced. The HindIII/XhoI fragment of the plasmid pUC18/GAL1-pp/afp, comprising the promoter GAL1, pre-pro region of secretion of MFα1 and encoding part of the human AFP gene (FIG. 2) were transferred to the HindIII/XhoI bireplicon (yeast—*E. coli*) vector pPDX. As a result the plasmid pPDX/GAL1-pp/afp was obtained. The ClaI/XhoI fragment of the plasmid pPDX/GAL1-pp/afp was transferred to ClaI/XhoI vector of pPK, differing from pPDX by the presence of the KAR2 gene. The plasmid obtained as a result is named pKX (FIG. 1). In a similar manner the plasmid pKX-1 was obtained, comprising the synthetic human AFP gene consisting of the most widely used yeast codons (FIG. 3). The plasmid pKX-1 differs from pKX in that it comprises the synthetic gene of a mature human AFP.

Example 4

Obtainment of a Strain-Producer of Human AFP

In order to obtain the strain *Saccharomyces cerevisiae* YBS723/pKX, the recipient strain YBS723 was transformed by the plasmid pKX in accordance with the method (Ito H., et al., 1983; J. Bacteriol. 153: 163-168). The transformants were selected by the capability to grow on a full-value yeast medium (bactopepton—20 g/l, yeast extract—10 g/l, bactoagar—20 g/l), comprising 2% glucose as the source of carbon. One of such clones is designated YBS723/pKX.

Example 5

Figure 4:
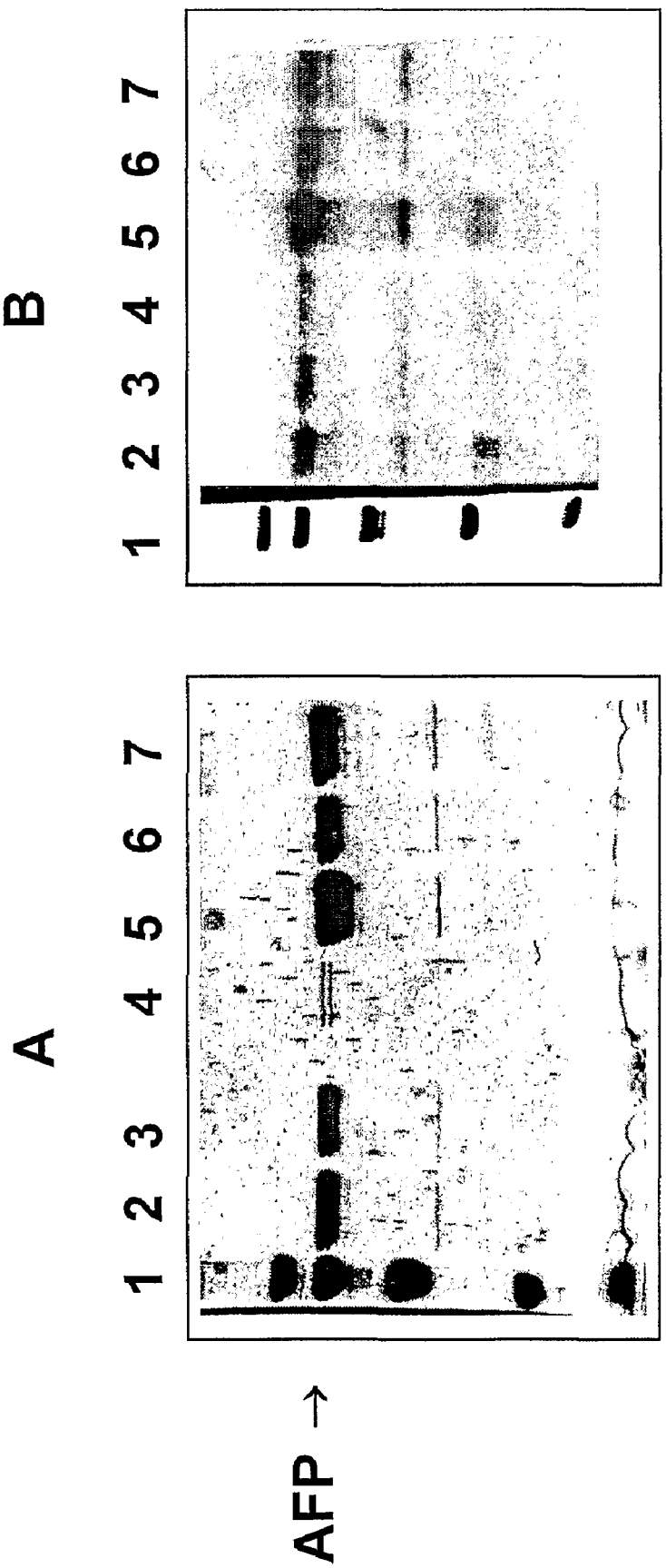
FIG. 4 shows the results of SDS-PAGE electroforesis (A) and immunoblotting-analysis (B) of different amounts, applied onto a line, of a purified recombinant alpha-fetoprotein obtained from a yeast culture *Saccharomyces cerevisiae* YBS723/pKX cultural liquid.

Determination of Productivity of Strain-Producer of Human AFP *Saccharomyces cerevisiae* YBS723/pKX Cells of the strain-producer YBS723/pKX were grown in vials at 26° C. on a rocker (250 rpm) on a medium of the following composition: glucose—2%, glycerine—1.5%, yeast extract—1%, peptone—2%, distilled water. The pH of the medium was maintained at 7.0 by the addition of 0.1 M of a phosphate buffer. The initial titer of the cells was 5×10$^6$. Samples were taken after 72 hours of growth of the culture after transition to the stationary phase of growth at a titer of 7-8×10$^8$. A sample of the cultural liquid was obtained after centrifugation of the culture at 10 000 rpm for 1 min and was used in the following analyses. Samples of the CL were analyzed by electrophoresis in a 12.5% polyacrylamide gel with sodium dodecyl sulphate. The gels were colored Coomassie R-250 (FIG. 4) and scanned to determine the total protein and relative content of the AFP specific protein. According to the data of electrophoresis and scanning, the total content of AFP in the CL is about 10-25% of the total protein, but there is partial intracellular degradation of the protein. The relative content of AFP in the CL was determined by the method of immunoblotting in the presence of polyclonal antibodies to AFP (FIG. 4). Also, the quantitative content of AFP in the cultural liquid was determined by the method of immunoenzymatic analysis (IEA), with use of a set of monoclonal and polyclonal antibodies to human AFP. According to the IEA data, the average content of AFP in the CL in liquid mediums reached 5 mg/l.

Example 6

Determination of Productivity of Strain-Producer of Human AFP *Saccharomyces cerevisiae* YBS723/pKX in High-Density Mediums Feed-batch culturing of the strain YBS723/pKX was carried out in a fermenter at 26° C. and pH 7.0 (automatic maintenance). The content of dissolved oxygen dO was maintained >20%. During fermentation, replenishment with a medium of the following composition was carried out: yeast extract—30 g/l, peptone—60 g/l, glucose—100 g/l.

The rate of feeding the replenishment was such as to provide a rate of growth of the culture $\mu$=0.03. After achievement of $OD_{50}$, equal to 280 optical units, the content of AFP in the CL was analyzed. The relative and total content of AFP in the CL of high density cultures of YBS723/pKX was determined as described above in example 4. In the case of culturing in high density mediums, the content of rAFP in the CL according to IFA data reached 70 mg/l.

Example 7

Isolation and Characterization of Recombinant Human AF from CL of a Strain-Producer YBS723/pKX Isolation of rAFP from the CL of the strain-producer YBS723/pKX was carried out as described earlier (Dudich et al., 1999, Biochemistry, 38:10406-10414) with slight changes. The cultural liquid was concentrated from 3 l to 200 ml by ultrafiltration on a concentrating cell "Millipore" and dialyzed against 0.005M Tris-HCl, a pH 7.5, 0.1M NaCl buffer, 4° C., then centrifuged for 0.5 hours at 10 000 rpm.

Ion exchange chromatography. The supernatant obtained after centrifugation was applied onto an ion exchange column DEAE-Sepharose Fast Flow (Pharmacia, 27×4 cm), balanced with 0.01M Tris-HCl, pH 7.5, 0.1M NaCl. The components not bond to sorbent were washed from the column with a starting buffer, while the elution of the desired product was carried out by 0.2 M of NaCl in a Tris-HCl buffer, pH 7.5 at a rate of 1 mL/min.

Affinity chromatography. The fractions comprising rAFP were combined, the concentration of NaCl was brought to 0.5M and applied to an affinity column with Sepharose CL-4B conjugated with polyclonal anti-AFP rabbit antibodies, which was balanced with 0.05M Tris-HCl, pH 7.5 and 0.5M NaCl. After the output of the proteins not bonded to the antibodies of the proteins, the adsorbed rAFP was eluted with 0.005M HCl. The peak of the output of the material upon achievement of pH from 5.0 to 3.5 was determined by absorption at 280 nm. The solution of rAFP was neutralized to pH 7.5 by the addition of a 2M solution of Tris-HCl, pH 7.5.

Gel chromatography. Further purification of rAFP was carried out by gel chromatography on a column with Sephacryl S-200 (1.8×70 cm) in a 0.1 M phosphate buffer, pH 7.0; 0.15M NaCl, at a rate of 0.5 ml/min. The solution of purified rAFP was concentrated in a cell "Amicon" (membrane YM-30) under the pressure of nitrogen.

Analysis of samples. The identification and purity of the obtained rAFP preparation were controlled by methods of gel electrophoresis according to Lammly in 12.5% SDS-PAGE with β-mercaptoethanol with subsequent coloring by Coomassie (FIG. 4A), Western-blot-analysis on a PVDF-membrane with a titer of primary antibodies 1:500 and secondary 1:5000, dot-blot on a Hybond ECL-nitrocellulose membrane (FIG. 4B), IFA.

Determination of the concentration of the protein in the solutions was canied out in accordance with the Bredford method, using a standard solution of embryonal AFP as the control, and also spectrophotometrically at 278 nm, talting the coefficient of extinction $E_{1\%,\ 278\ nm}$=0.53 into account.

Example 8

Determination of Biological Activity of Recombinant Human AFP In Vitro

The functional activity of rAFP and the modified forms thereof were determined according to its capability of suppressing the growth of cells of B-cellular lymphoma Raji in the culture in vitro, as earlier described (Semenkova L. N., 1997, Tumor Biol. 18, 261-274; Dudich E. I., et al., 1998, Tumor Biol. 19, 30-40). Preliminarily washed by a fresh medium, Raji cells were placed into each cell of a 96-alveolar plate according to $5 \times 10^3$ in 0.1 ml of a medium RPMI-1640 in the presence of a 10% fetal calf serum, then different doses of AFP were added for 12 hours. Proliferation of the cells was measured by a standard method by the introduction of $[H^3]$-thymidine during the last 4 hours of culturing. For comparison, the dose-dependent reactivity was studied for two samples of AFP of embryonal origin embrAFP and yeast rAFP (FIG. 5). It is evident that both preparations manifest an expressed cytostatic activity in respect to these cells. Similarly, in order to determine the activity of preparations on the base of AFP in vitro, any other lines of cancer cells may be used that are sensitive to the suppressive action of AFP, such as human hepatocarcinoma HepG2, breast cancer MCF-7, prostate cancer LnCap, myeloblastoma U-937 and others (Semenkova L. N., 1997, Tumor Biol. 18, 261-274; Dudich E. I., et al., 1998, Tumor Biol. 19, 30-40).

Example 9A

Use of Recombinant AFP as Anticancer Preparation

Anticancer preparations on the base of rAFP and of modified forms thereof may be used for inhibition of the growth of malignant neoplasms, such as primary or metastatic cancer of the liver, blood cancer (leucosis, myeloblastoma, lymphoma), breast cancer, prostate cancer. In order to determine the sensitivity of this type of tumor cells to AFP, it is possible to use different methods both in vitro and also in vivo. The method of determining activity in vitro is described in the preceding example 8. In order to determine the oncosuppressive action of preparations on the base of AFP in vivo, models on animals may be used, for example with use of Nude mice with subcutaneously or intraperitoneally implanted human lines of cancer cells, such as Raji, HepG2, LnCap, MCF-7 and others. For example, cells of B-cellular lymphoma Raji were administered subcutaneously in an amount of 1-5×10$^6$ per mouse. Administration of the AFP and derivatives thereof was begun 7 days prior to implantation of tumor cells intraperitoneally or intravenously in an amount of 1-10 mg/kg. The physiological buffered solution (PBS) was used as a control. The size of the tumor was evaluated by daily measurements with the aid of a micrometer.

TABLE 1

Results of tests of rAFP on models of Nude line mice implanted with cells of B-cellular lymphoma Raji

| Number of animals | Dose of AFP per injection | Method of administration | Result |
| --- | --- | --- | --- |
| 10 | 1 mg | Intraperitoneally, daily for 20 days | 2 - stabilization 5 - 50% inhibition 3 - tumor did not develop |
| 5 | PBS | Intraperitoneally, daily for 20 days | 10 - 100% development of tumor |
| 10 | 0.5 mg | Intraperitoneally, daily for 20 days | 2 - stabilization 5 - 50% inhibition 3 - tumor did not develop |
| 10 | 2 mg | Intraperitoneally, daily for 20 days | 2 - stabilization 5 - 50% inhibition 3 - tumor did not develop |

The method of administering preparations on the base of yeast rAFP or derivatives thereof may also comprise therein the administration of chemotherapeutic preparations simultaneously or sequentially. The following may be presented as examples of such chemotherapeutic preparations: doxorubicin, vincristine, fluorourascil, metatrexate, actinomycin D, mitomycin C, tamoxifen, flutamid, vincristine, vinblastine, cyclosporin, retinoids, carotenoids, and others. Usually, a chemotherapeutic preparation may be administered in standard doses or in suboptimum doses, below the usual therapeutic. The effect of the combined action of rAFP and doxorubicin (A) and rAFP and all-trans-Retinoic acid (tRA) is presented as an example in FIG. 6. In the case of simultaneous administration of the preparations, synergic oncosuppressive action in the case of use of suboptimum doses is observed.

Example 9B

Use of Recombinant AFP for Stimulation of the Growth of Stem Cells

The primary culture of embryonal fibroblasts of the lung and human retina was obtained by treating with a 0.2% trypsin solution corresponding tissues of 5-10 week embryos obtained after legal abortions. The cells were cultured in an RPMI-1640 medium in the presence of a 10% calf fetal serum (CFS). The cytostatic activity of AFP was measured as earlier described (Semenkova L. N., 1997, Tumor Biol. 18, 261-274; Dudich E. I., et al., 1998, Tumor Biol. 19, 30-40). Cells in an amount of 4×10$^4$ in a 0.15 ml medium were intensively washed with a fresh medium and placed in each cell of a 96-lune plate, then different doses of AFP were added and cultured 24 hours. Proliferation of the cells was measured by a standard method by the inclusion of [H$^3$]-thymidine during the last four hours of culturing.

The dosage dependence of the effect of AFP on cellular growth was also studied for the primary culture of human embryonal fibroblasts. AFP had a stimulating effect on these cells, reaching 50-90% in respect to the control (FIG. 7).

Example 10

Use of Recombinant AFP in Cosmetology

In view of the fact that AFP has the capability to stimulate the growth of stem cells and is a growth factor for embryonal cells, its possible use is proposed for the preparation of cosmetic masks, creams and lotions. rAFP may be used as an excipient for liposome, microsome and nanosome. In view of the fact that AFP is capable of binding hydrophobic ligands, in particular, fat-soluble vitamins, steroids, isoflavinoids, polyunsaturated fatty acids (Deutsch H. F., 1991, Adv. Canc. Res. 56, 253-312); Aussel C. & Masseyeff R., 1994, Biochem. Biophys. Res. Commun. 119: 1122-1127; Deutsch H. F., 1994, J. Tumor Marker Oncol. 9: 11-14), the combined use of rAFP with fat-soluble vitamins, such as derivatives of retinoids, carotenoids, tokoferol, vitamin D, with steroids such as derivatives of estrogens and androgens, is shown. Estradiol and others may be used as an example of such steroids.

REFERENCES

Amaim E., Ochs B., Abel K.-J. (1988) Tightly regulated tac promoter vectors useful for the expression of unfused and fused proteins in *Escherichia coli*. Gene. 69(2):301-15.

Aussel, C. & Masseyeff, R. (1994) Interaction of retinoids and bilirubin with the binding of arachidonic acid to human alpha-fetoprotein. Biochem. Biophys. Res. Commun. 119, 1122-1127.

Bennett, J. A., Semeniuk, D. J., Jacobson, H. I. & Murgita, R. A. (1997) Similarity between natural and recombinant human alpha-fetoprotein as inhibitors of estrogen-dependent breast cancer growth. Breast Cancer Res. Treat. 45, 169-179

Bennet, J. A., Zhu, S., Pagano-Mirarchi, A., Kellom, T. A. & Jacobson, H. I. (1998) α-Fetoprotein derived from a human hepatoma prevents growth of estrogen-dependent human breast cancer xenografts. Clinical Cancer Research, 4, 2877-2884.

Boismenu R., Semeniulc D., Murgita R. A. (1997) Purification and characterization of human and mouse recombinant alpha-fetoproteins expressed in *Echerichia coli*. Protein Expression and Purification. 10:10-26.

Chung B. H., Park K. S. (1998) A simple approach to reducing the proteolysis during the secretory production of human parathyroid hormone in *Saccharomyces cerevisiae*. Biotechnol. Bioeng. 57:245-249.

Deutsch, H. F. (1991) Chemistry and biology of x-fetoprotein. Adv. Canc. Res. 56, 253-312.

Deutsch H. F. (1994) The uptake of adriamycin-arachidonic acid complexes by human tumor cells in the presence of α-fetoprotein. J. Tumor Marker Oncol. 9: 11-14.

Dudich, E. I., Semenkova, L. N., Gorbatova, E. A., Dudich, I. V., Khromykh, L. M., Tatulov, E. B., Grechko, G. K. & Sukhikh, G. T. (1998) Growth-regulative activity of alpha-fetoprotein for different types of tumor and normnal cells. Tumor Biol. 19, 30-40.

Dudich E. I., Semenkova L. N., Dudich I. V., Gorbatova E. A., Tokhtamysheva, N., Tatulov E. B., Nikolaeva M. A. & Sukhikh G. T. (1999) α-Fetoprotein causes apoptosis in tumor cells via a pathway independent of CD95, TNFR1 and TNFR2 through activation of caspase-3-like proteases. Eur. J. Biochem., 266:1-13

Dudich, I. V., Tokhtamysheva, N., Semenkova, L., Dudich, E., Hellman, J. and Korpela, T. (1999) Isolation and structural and functional characterization of two stable peptic fragments of human alpha-fetoprotein. Biochemistry, 38: 10406-10414.

Ito H., Fukuda Y., Murata K., Kimura A. (1983) Transformation of intact yeast cells treated with alkali cations. J. Bacteriol. 1983, 153:163-168.

Hard K, Bitter W, Kamerling J P, Vliegenthart J F. (1989) O-mannosylation of recombinant human insulin-like growth factor I (IGF-I) produced in Saccharomyces cerevisiae. FEBS Lett. 248:111-4.

Quirk A. Y., Geisow M. J., Woodrow J. R., Burton S. J., Wood P. C., Sutton A. D., Lohnson R. A., Dodsworth N. (1989) Production of recombinant human serum albumin from Saccharomyces cerevisiae. Bitechnol. Appl. Biochem. 11: 273-287.

Kang H. A., Choi E. S., Hong W. K., Kim J. Y., Ko S. M., Sohn J. H., Rhee S. K. (2000) Proteolytic stability of recombinant human serum albumin secreted in the yeast Saccharomyces cerevisiae. Appl. Microbiol. Biotechnol. 53: 575-582.

Mizejewsky G. J. (2002) Biological role of x-fetoprotein in cancer: prospects for anticancer therapy. Expert Rev. Anticancer. Ther. 2: 89-115.

Morinaga, T., Sakai, M., Wegmann, T. G., and Namaoki, T. (1983) Primary structures of human α-fetoprotein and its mRNA. Proc. Natl. Acad. Sci. U.S.A. 80, 4604-4608.

Murgita R., Recombinant human alpha-fetoprotein as an immunosuppressive agent. U.S. Pat. No. 5,965,528 C07K 14/47, 1999.

Murgita R., Recombinant human alpha-fetoprotein as a cell proliferative agent U.S. Pat. No. 6,627,440 C12N 005/00, 2003.

Murgita R., Recombinant alpha-fetoprotein for treating and diagnosing cancers U.S. Pat. No. 6,416,734, A61K 051/00, 2002.

Murgita R. A. Expression and purification of cloned human alpha-fetoprotein. U.S. Pat. No. 6,331,611 C07K 014/00, 2001.

Nishi S., Koyama Y., Sakamoto T., Soda M., Kairiyama C. B. (1988) Expression of rat α-fetoprotein cDNA Esherichia coli and in yeast. J. Biochem. 104: 968-972.

Pucci, P., Siciliano, R., Maiorni, A., Marino, G., Tecce, M., F., Ceccarini, C., and Terrana, B. (1991) Biochemistry 30:5061-5066.

Uriel J., Laborda J., Naval J., Geuskens M (1989) Alpha-fetoprotein receptors in malignant cells. An overview; in Mizejewsky G. I., Jakobson H. I. (eds): Biological Properties of Alpha-Fetoprotein. Boca Raton, CRC Press, vol. 2:103-117.

Robinson A. S., Bockhaus J. A., Witthup K. D. (1996) Reduction of BiP level decreases heterologous protein secretion in Saccharomyces cerevisiae. J. Biol. Chem. 271:10017-10022.

Semenkova, L. N., Dudich, E. I. & Dudich, I. V. (1997) Induction of apoptosis in human hepatoma cells by alpha-fetoprotein. Tumor Biol. 18, 261-274.

Semenkova, L., Dudich, E., Dudich, I., Tokhtamisheva, N., Tatulov, E., Okruzhnov, Y., Garcia-Foncillas, J., Palop-Cubillo J.-A., Korpela T. (2003) Alpha-fetoprotein positively regulates cytochrome c-mediated caspase activation and apoptosome complex formation, Eur. J. Biochem. 70: 4388-4399.

Sleep D., Belfield G. P., Goodey A. R. (1990) The secretion of human serum albumin from the yeast Saccharomyces cerevisiae using five different leader sequences. Biotechnology 8: 42-46.

Shusta E. V., Raines R. T., Pluckthun A., Wittrup K. D. (1998) Increasing the secretory capacity of Saccharomyces cerevisiae for production of single-chain antibody fragment. Nature Biotechnol. 16: 773-777.

Tamaoki T., Morinaga T., Nishi S. (1993) Method of producing human .alpha.-fetoprotein and product produced thereby. U.S. Pat. No. 5,206,153, C07K 013/00; C12N 015/62.

Tsukada Y., Hibi N., Ohlcawa K., Deutsch H. F. (1994) Cytocidal effect of daunomycin unsaturated fatty acid complexes on rat tumor cell lines. J. Tumor Marker Oncol. 9: 99-103.

Yamashita, K., Taketa, K., Nishi, S., Fukushima K., and Ohkura T. (1993) Sugar chains of human cord serum α-fetoprotein. Cancer Res. 53, 2970-2975.

Yamamoto R., Sakamoto T., Nishi S., Sakai M., Morinaga T., Tamaoki T. (1990) Expression of human α-fetoprotein in yeast. Life Sciences, 46:1679-1686.

The invention claimed is:

1. An expression cassette for expressing recombinant mature human alpha-fetoprotein, wherein the cassette comprises the nucleic acid sequence of SEQ ID NO: 1.

2. A recombinant plasmid comprising: the expression cassette of claim 1; a fragment of the bacterial plasmid pUC18; a region of initiation of replication of a 2-μm yeast plasmid; a KAR2 gene; a PDII gene; a selective URA3 yeast marker; and a selective PGK1 yeast marker.

3. A eukaryotic cell transformed with the plasmid according to claim 2.

4. A method for preparing recombinant mature human alpha-fetoprotein comprising: (a) culturing the eukaryotic cell of claim 3 in culture medium, wherein the cell secretes recombinant mature human alpha-fetoprotein into the culture medium, and (b) isolating the recombinant mature human alpha-fetoprotein from the culture medium.

5. The method according to claim 4, wherein the eukaryotic cell is a yeast cell.

6. The method according to claim 5, wherein the yeast cell is a cell of a strain of *Saccharomyces cerevisiae*.

* * * * *

UNITED STATES PATENT AND TRADEMARK OFFICE
CERTIFICATE OF CORRECTION

PATENT NO. : 7,910,327 B2
APPLICATION NO. : 11/632409
DATED : March 22, 2011
INVENTOR(S) : Sergei Benevolensky et al.

Page 1 of 1

It is certified that error appears in the above-identified patent and that said Letters Patent is hereby corrected as shown below:

IN THE CLAIMS:
Column 35, Claim 2, line 35 replace "a PDII gene" with --a PDI1 gene--.

Signed and Sealed this
Sixteenth Day of August, 2011

David J. Kappos
Director of the United States Patent and Trademark Office

SEQUENCE LISTING

```
<160> NUMBER OF SEQ ID NOS: 9

<210> SEQ ID NO 1
<211> LENGTH: 2556
<212> TYPE: DNA
<213> ORGANISM: Artificial Sequence
<220> FEATURE:
<223> OTHER INFORMATION: chemically synthesized
<220> FEATURE:
<221> NAME/KEY: CDS
<222> LOCATION: (529)..(2553)

<400> SEQUENCE: 1
aagctttagc ctaaaaaaac cttctctttg gaactttcag taatacgctt aactgctcat      60
tgctatattg aagtacggat tagaagccgc cgagcgggtg acagccctcc gaaggaagac     120
tctcctccgt gcgtcctcgt cttcaccggt cgcgttcctg aaacgcagat gtgcctcgcg     180
ccgcactgct ccgaacaata aagattctac aatactagct tttatggtta tgaagaggaa     240
```

```
aaaattggcag taacctggcc ccacaaacct tcaaatgaac gaatcaaatt aacaaccata      300
ggatgataat gcgattagtt ttttagcctt atttctgggg taattaatca gcgaagcgat      360
gatttttgat ctattaacag atatataaat gcaaaaactg cataaccact ttaactaata      420
ctttcaacat tttcggtttg tattacttct tattcaaatg taataaaagt atcaacaaaa      480
aattgttaat atacctctat actttaacgt caaggagaaa aaactacc atg aga ttt       537
                                                    Met Arg Phe
                                                     1
```

| | | | | | | | | | | | | | | | | |
|---|---|---|---|---|---|---|---|---|---|---|---|---|---|---|---|---|
| cca | tct | atc | ttc | act | gca | gtt | tta | ttc | gca | gca | tcc | tcc | gca | tta | gct | 585 |
| Pro | Ser | Ile | Phe | Thr | Ala | Val | Leu | Phe | Ala | Ala | Ser | Ser | Ala | Leu | Ala | |
| 5 | | | | 10 | | | | | 15 | | | | | | | |
| gct | cca | gtc | aac | act | aca | aca | gaa | gat | gaa | acg | gca | caa | att | ccg | gct | 633 |
| Ala | Pro | Val | Asn | Thr | Thr | Thr | Glu | Asp | Glu | Thr | Ala | Gln | Ile | Pro | Ala | |
| 20 | | | | 25 | | | | 30 | | | | | | 35 | | |
| gaa | gct | gtc | atc | ggt | tac | tta | gat | tta | gaa | ggg | gat | ttc | gat | gtt | gct | 681 |
| Glu | Ala | Val | Ile | Gly | Tyr | Leu | Asp | Leu | Glu | Gly | Asp | Phe | Asp | Val | Ala | |
| 40 | | | | 45 | | | | 50 | | | | | | | | |
| gtt | ttg | cca | ttt | tcc | aac | agc | aca | aat | aac | ggg | tta | ttg | ttt | ata | aat | 729 |
| Val | Leu | Pro | Phe | Ser | Asn | Ser | Thr | Asn | Asn | Gly | Leu | Leu | Phe | Ile | Asn | |
| 55 | | | | 60 | | | | 65 | | | | | | | | |
| act | act | att | gcc | agc | att | gct | gct | aaa | gaa | gaa | ggg | gta | tcc | atg | gct | 777 |
| Thr | Thr | Ile | Ala | Ser | Ile | Ala | Ala | Lys | Glu | Glu | Gly | Val | Ser | Met | Ala | |
| 70 | | | | 75 | | | | 80 | | | | | | | | |
| aaa | agg | aca | ctg | cat | aga | aat | gaa | tat | gga | ata | gct | tcc | ata | ttg | gat | 825 |
| Lys | Arg | Thr | Leu | His | Arg | Asn | Glu | Tyr | Gly | Ile | Ala | Ser | Ile | Leu | Asp | |
| 85 | | | | 90 | | | | 95 | | | | | | | | |
| tct | tac | caa | tgt | act | gca | gag | ata | agt | tta | gct | gac | ctg | gct | acc | ata | 873 |
| Ser | Tyr | Gln | Cys | Thr | Ala | Glu | Ile | Ser | Leu | Ala | Asp | Leu | Ala | Thr | Ile | |
| 100 | | | | 105 | | | | 110 | | | | | | 115 | | |
| ttt | ttt | gcc | cag | ttt | gtt | caa | gaa | gcc | act | tac | aag | gaa | gta | agc | aaa | 921 |
| Phe | Phe | Ala | Gln | Phe | Val | Gln | Glu | Ala | Thr | Tyr | Lys | Glu | Val | Ser | Lys | |
| 120 | | | | 125 | | | | 130 | | | | | | | | |
| atg | gtg | aaa | gat | gca | ttg | act | gca | att | gag | aaa | ccc | act | gga | gat | gaa | 969 |
| Met | Val | Lys | Asp | Ala | Leu | Thr | Ala | Ile | Glu | Lys | Pro | Thr | Gly | Asp | Glu | |
| 135 | | | | 140 | | | | 145 | | | | | | | | |
| cag | tct | tca | ggg | tgt | tta | gaa | aac | cag | cta | cct | gcc | ttt | ctg | gaa | gaa | 1017 |
| Gln | Ser | Ser | Gly | Cys | Leu | Glu | Asn | Gln | Leu | Pro | Ala | Phe | Leu | Glu | Glu | |
| 150 | | | | 155 | | | | 160 | | | | | | | | |
| ctt | tgc | cat | gag | aaa | gaa | att | ttg | gag | aag | tac | gga | cat | tca | gac | tgc | 1065 |
| Leu | Cys | His | Glu | Lys | Glu | Ile | Leu | Glu | Lys | Tyr | Gly | His | Ser | Asp | Cys | |
| 165 | | | | 170 | | | | 175 | | | | | | | | |
| tgc | agc | caa | agt | gaa | gag | gga | aga | cat | aac | tgt | ttt | ctt | gca | cac | aaa | 1113 |
| Cys | Ser | Gln | Ser | Glu | Glu | Gly | Arg | His | Asn | Cys | Phe | Leu | Ala | His | Lys | |
| 180 | | | | 185 | | | | 190 | | | | | | 195 | | |
| aag | ccc | act | cca | gca | tcg | atc | cca | ctt | ttc | caa | gtt | cca | gaa | cct | gtc | 1161 |
| Lys | Pro | Thr | Pro | Ala | Ser | Ile | Pro | Leu | Phe | Gln | Val | Pro | Glu | Pro | Val | |
| 200 | | | | 205 | | | | 210 | | | | | | | | |
| aca | agc | tgt | gaa | gca | tat | gaa | gaa | gac | agg | gag | aca | ttc | atg | aac | aaa | 1209 |
| Thr | Ser | Cys | Glu | Ala | Tyr | Glu | Glu | Asp | Arg | Glu | Thr | Phe | Met | Asn | Lys | |
| 215 | | | | 220 | | | | 225 | | | | | | | | |
| ttc | att | tat | gag | ata | gca | aga | agg | cat | ccc | ttc | ctg | tat | gca | cct | aca | 1257 |
| Phe | Ile | Tyr | Glu | Ile | Ala | Arg | Arg | His | Pro | Phe | Leu | Tyr | Ala | Pro | Thr | |
| 230 | | | | 235 | | | | 240 | | | | | | | | |
| att | ctt | ctt | tgg | gct | gct | cgc | tat | gac | aaa | ata | att | cca | tct | tgc | tgc | 1305 |
| Ile | Leu | Leu | Trp | Ala | Ala | Arg | Tyr | Asp | Lys | Ile | Ile | Pro | Ser | Cys | Cys | |
| 245 | | | | 250 | | | | 255 | | | | | | | | |
| aaa | gct | gaa | aat | gca | gtt | gaa | tgc | ttc | caa | aca | aag | gca | gca | aca | gtt | 1353 |
| Lys | Ala | Glu | Asn | Ala | Val | Glu | Cys | Phe | Gln | Thr | Lys | Ala | Ala | Thr | Val | |
| 260 | | | | 265 | | | | 270 | | | | | | 275 | | |

| | | | | | | | | | | | | | | | | |
|---|---|---|---|---|---|---|---|---|---|---|---|---|---|---|---|---|
| aca | aaa | gaa | tta | aga | gaa | agc | agc | ttg | tta | aat | caa | cat | gca | tgt | gca | 1401 |
| Thr | Lys | Glu | Leu | Arg | Glu | Ser | Ser | Leu | Leu | Asn | Gln | His | Ala | Cys | Ala | |
| 280 | | | | | 285 | | | | | 290 | | | | | | |
| gta | atg | aaa | aat | ttt | ggg | acc | cga | act | ttc | caa | gcc | ata | act | gtt | act | 1449 |
| Val | Met | Lys | Asn | Phe | Gly | Thr | Arg | Thr | Phe | Gln | Ala | Ile | Thr | Val | Thr | |
| 295 | | | | | 300 | | | | | 305 | | | | | | |
| aaa | ctg | agt | cag | aag | ttt | acc | aaa | gtt | aat | ttt | act | gaa | atc | cag | aaa | 1497 |
| Lys | Leu | Ser | Gln | Lys | Phe | Thr | Lys | Val | Asn | Phe | Thr | Glu | Ile | Gln | Lys | |
| 310 | | | | | 315 | | | | | 320 | | | | | | |
| cta | gtc | ctg | gat | gtg | gcc | cat | gta | cat | gag | cac | tgt | tgc | aga | gga | gat | 1545 |
| Leu | Val | Leu | Asp | Val | Ala | His | Val | His | Glu | His | Cys | Cys | Arg | Gly | Asp | |
| 325 | | | | | 330 | | | | | 335 | | | | | | |
| gtg | ctg | gat | tgt | ctg | cag | gat | ggg | gaa | aaa | atc | atg | tcc | tac | ata | tgt | 1593 |
| Val | Leu | Asp | Cys | Leu | Gln | Asp | Gly | Glu | Lys | Ile | Met | Ser | Tyr | Ile | Cys | |
| 340 | | | | | 345 | | | | | 350 | | | | | 355 | |
| tct | caa | caa | gac | act | ctg | tca | aac | aaa | ata | aca | gaa | tgc | tgc | aaa | ctg | 1641 |
| Ser | Gln | Gln | Asp | Thr | Leu | Ser | Asn | Lys | Ile | Thr | Glu | Cys | Cys | Lys | Leu | |
| 360 | | | | | 365 | | | | | 370 | | | | | | |
| acc | acg | ctg | gaa | cgt | ggt | caa | tgt | ata | att | cat | gca | gaa | aat | gat | gaa | 1689 |
| Thr | Thr | Leu | Glu | Arg | Gly | Gln | Cys | Ile | Ile | His | Ala | Glu | Asn | Asp | Glu | |
| 375 | | | | | 380 | | | | | 385 | | | | | | |
| aaa | cct | gaa | ggt | cta | tct | cca | aat | cta | aac | agg | ttt | tta | gga | gat | aga | 1737 |
| Lys | Pro | Glu | Gly | Leu | Ser | Pro | Asn | Leu | Asn | Arg | Phe | Leu | Gly | Asp | Arg | |
| 390 | | | | | 395 | | | | | 400 | | | | | | |
| gat | ttt | aac | caa | ttt | tct | tca | ggg | gaa | aaa | aat | atc | ttc | ttg | gca | agt | 1785 |
| Asp | Phe | Asn | Gln | Phe | Ser | Ser | Gly | Glu | Lys | Asn | Ile | Phe | Leu | Ala | Ser | |
| 405 | | | | | 410 | | | | | 415 | | | | | | |
| ttt | gtt | cat | gaa | tat | tca | aga | aga | cat | cct | cag | ctt | gct | gtc | tca | gta | 1833 |
| Phe | Val | His | Glu | Tyr | Ser | Arg | Arg | His | Pro | Gln | Leu | Ala | Val | Ser | Val | |
| 420 | | | | | 425 | | | | | 430 | | | | | 435 | |
| att | cta | aga | gtt | gct | aaa | gga | tac | cag | gag | tta | ttg | gag | aag | tgt | ttc | 1881 |
| Ile | Leu | Arg | Val | Ala | Lys | Gly | Tyr | Gln | Glu | Leu | Leu | Glu | Lys | Cys | Phe | |
| 440 | | | | | 445 | | | | | 450 | | | | | | |
| cag | act | gaa | aac | cct | ctt | gaa | tgc | caa | gat | aaa | gga | gaa | gaa | gaa | tta | 1929 |
| Gln | Thr | Glu | Asn | Pro | Leu | Glu | Cys | Gln | Asp | Lys | Gly | Glu | Glu | Glu | Leu | |
| 455 | | | | | 460 | | | | | 465 | | | | | | |
| cag | aaa | tac | atc | cag | gag | agc | caa | gca | ttg | gca | aag | cga | agc | tgc | ggc | 1977 |
| Gln | Lys | Tyr | Ile | Gln | Glu | Ser | Gln | Ala | Leu | Ala | Lys | Arg | Ser | Cys | Gly | |
| 470 | | | | | 475 | | | | | 480 | | | | | | |
| ctc | ttc | cag | aaa | cta | gga | gaa | tat | tac | tta | caa | aat | gcg | ttt | ctc | gtt | 2025 |
| Leu | Phe | Gln | Lys | Leu | Gly | Glu | Tyr | Tyr | Leu | Gln | Asn | Ala | Phe | Leu | Val | |
| 485 | | | | | 490 | | | | | 495 | | | | | | |
| gct | tac | aca | aag | aaa | gcc | ccc | cag | ctg | acc | tcg | tcg | gag | ctg | atg | gcc | 2073 |
| Ala | Tyr | Thr | Lys | Lys | Ala | Pro | Gln | Leu | Thr | Ser | Ser | Glu | Leu | Met | Ala | |
| 500 | | | | | 505 | | | | | 510 | | | | | 515 | |
| atc | acc | aga | aaa | atg | gca | gcc | aca | gca | gcc | act | tgt | tgc | caa | ctc | agt | 2121 |
| Ile | Thr | Arg | Lys | Met | Ala | Ala | Thr | Ala | Ala | Thr | Cys | Cys | Gln | Leu | Ser | |
| 520 | | | | | 525 | | | | | 530 | | | | | | |
| gag | gac | aaa | cta | ttg | gcc | tgt | ggc | gag | gga | gcg | gct | gac | att | att | atc | 2169 |
| Glu | Asp | Lys | Leu | Leu | Ala | Cys | Gly | Glu | Gly | Ala | Ala | Asp | Ile | Ile | Ile | |
| 535 | | | | | 540 | | | | | 545 | | | | | | |
| gga | cac | tta | tgt | atc | aga | cat | gaa | atg | act | cca | gta | aac | cct | ggt | gtt | 2217 |
| Gly | His | Leu | Cys | Ile | Arg | His | Glu | Met | Thr | Pro | Val | Asn | Pro | Gly | Val | |
| 550 | | | | | 555 | | | | | 560 | | | | | | |
| ggc | cag | tgc | tgc | act | tct | tca | tat | gcc | aac | agg | agg | cca | tgc | ttc | agc | 2265 |
| Gly | Gln | Cys | Cys | Thr | Ser | Ser | Tyr | Ala | Asn | Arg | Arg | Pro | Cys | Phe | Ser | |
| 565 | | | | | 570 | | | | | 575 | | | | | | |
| agc | ttg | gtg | gtg | gat | gaa | aca | tat | gtc | cct | cct | gca | ttc | tct | gat | gac | 2313 |
| Ser | Leu | Val | Val | Asp | Glu | Thr | Tyr | Val | Pro | Pro | Ala | Phe | Ser | Asp | Asp | |
| 580 | | | | | 585 | | | | | 590 | | | | | 595 | |

-continued

```
aag ttc att ttc cat aag gat ctg tgc caa gct cag ggt gta gcg ctg    2361
Lys Phe Ile Phe His Lys Asp Leu Cys Gln Ala Gln Gly Val Ala Leu
600                 605                 610 caa acg atg aag caa gag ttt ctc att aac ctt gtg aag caa aag cca    2409
Gln Thr Met Lys Gln Glu Phe Leu Ile Asn Leu Val Lys Gln Lys Pro
615                 620                 625 caa ata aca gag gaa caa ctt gag gct gtc att gca gat ttc tca ggc    2457
Gln Ile Thr Glu Glu Gln Leu Glu Ala Val Ile Ala Asp Phe Ser Gly
630                 635                 640 ctg ttg gag aaa tgc tgc caa ggc cag gaa cag gaa gtc tgc ttt gct    2505
Leu Leu Glu Lys Cys Cys Gln Gly Gln Glu Gln Glu Val Cys Phe Ala
645                 650                 655 gaa gag gga caa aaa ctg att tca aaa act cgt gct gct ttg gga gtt    2553
Glu Glu Gly Gln Lys Leu Ile Ser Lys Thr Arg Ala Ala Leu Gly Val
660                 665                 670                 675 taa                                                                 2556
```

<210> SEQ ID NO 2
<211> LENGTH: 675
<212> TYPE: PRT
<213> ORGANISM: Artificial Sequence
<220> FEATURE:
<223> OTHER INFORMATION: Synthetic Construct

<400> SEQUENCE: 2

```
Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Met Ala Lys Arg Thr Leu His Arg Asn Glu Tyr Gly Ile Ala Ser
                85                  90                  95

Ile Leu Asp Ser Tyr Gln Cys Thr Ala Glu Ile Ser Leu Ala Asp Leu
            100                 105                 110

Ala Thr Ile Phe Phe Ala Gln Phe Val Gln Glu Ala Thr Tyr Lys Glu
        115                 120                 125

Val Ser Lys Met Val Lys Asp Ala Leu Thr Ala Ile Glu Lys Pro Thr
130                 135                 140

Gly Asp Glu Gln Ser Ser Gly Cys Leu Glu Asn Gln Leu Pro Ala Phe
145                 150                 155                 160

Leu Glu Glu Leu Cys His Glu Lys Glu Ile Leu Glu Lys Tyr Gly His
                165                 170                 175

Ser Asp Cys Cys Ser Gln Ser Glu Glu Gly Arg His Asn Cys Phe Leu
            180                 185                 190

Ala His Lys Lys Pro Thr Pro Ala Ser Ile Pro Leu Phe Gln Val Pro
        195                 200                 205

Glu Pro Val Thr Ser Cys Glu Ala Tyr Glu Glu Asp Arg Glu Thr Phe
210                 215                 220

Met Asn Lys Phe Ile Tyr Glu Ile Ala Arg Arg His Pro Phe Leu Tyr
225                 230                 235                 240

Ala Pro Thr Ile Leu Leu Trp Ala Ala Arg Tyr Asp Lys Ile Ile Pro
                245                 250                 255
```

```
Ser Cys Cys Lys Ala Glu Asn Ala Val Glu Cys Phe Gln Thr Lys Ala
        260                 265                 270
Ala Thr Val Thr Lys Glu Leu Arg Glu Ser Ser Leu Leu Asn Gln His
        275                 280                 285
Ala Cys Ala Val Met Lys Asn Phe Gly Thr Arg Thr Phe Gln Ala Ile
        290                 295                 300
Thr Val Thr Lys Leu Ser Gln Lys Phe Thr Lys Val Asn Phe Thr Glu
305                 310                 315                 320
Ile Gln Lys Leu Val Leu Asp Val Ala His Val His Glu His Cys Cys
                325                 330                 335
Arg Gly Asp Val Leu Asp Cys Leu Gln Asp Gly Glu Lys Ile Met Ser
                340                 345                 350
Tyr Ile Cys Ser Gln Gln Asp Thr Leu Ser Asn Lys Ile Thr Glu Cys
            355                 360                 365
Cys Lys Leu Thr Thr Leu Glu Arg Gly Gln Cys Ile Ile His Ala Glu
        370                 375                 380
Asn Asp Glu Lys Pro Glu Gly Leu Ser Pro Asn Leu Asn Arg Phe Leu
385                 390                 395                 400
Gly Asp Arg Asp Phe Asn Gln Phe Ser Ser Gly Glu Lys Asn Ile Phe
                405                 410                 415
Leu Ala Ser Phe Val His Glu Tyr Ser Arg Arg His Pro Gln Leu Ala
                420                 425                 430
Val Ser Val Ile Leu Arg Val Ala Lys Gly Tyr Gln Glu Leu Leu Glu
            435                 440                 445
Lys Cys Phe Gln Thr Glu Asn Pro Leu Glu Cys Gln Asp Lys Gly Glu
        450                 455                 460
Glu Glu Leu Gln Lys Tyr Ile Gln Glu Ser Gln Ala Leu Ala Lys Arg
465                 470                 475                 480
Ser Cys Gly Leu Phe Gln Lys Leu Gly Glu Tyr Tyr Leu Gln Asn Ala
                485                 490                 495
Phe Leu Val Ala Tyr Thr Lys Lys Ala Pro Gln Leu Thr Ser Ser Glu
                500                 505                 510
Leu Met Ala Ile Thr Arg Lys Met Ala Ala Thr Ala Ala Thr Cys Cys
            515                 520                 525
Gln Leu Ser Glu Asp Lys Leu Leu Ala Cys Gly Glu Gly Ala Ala Asp
        530                 535                 540
Ile Ile Ile Gly His Leu Cys Ile Arg His Glu Met Thr Pro Val Asn
545                 550                 555                 560
Pro Gly Val Gly Gln Cys Cys Thr Ser Ser Tyr Ala Asn Arg Arg Pro
                565                 570                 575
Cys Phe Ser Ser Leu Val Val Asp Glu Thr Tyr Val Pro Pro Ala Phe
                580                 585                 590
Ser Asp Asp Lys Phe Ile Phe His Lys Asp Leu Cys Gln Ala Gln Gly
            595                 600                 605
Val Ala Leu Gln Thr Met Lys Gln Glu Phe Leu Ile Asn Leu Val Lys
        610                 615                 620
Gln Lys Pro Gln Ile Thr Glu Glu Gln Leu Glu Ala Val Ile Ala Asp
625                 630                 635                 640
Phe Ser Gly Leu Leu Glu Lys Cys Cys Gln Gly Gln Glu Gln Glu Val
                645                 650                 655
Cys Phe Ala Glu Glu Gly Gln Lys Leu Ile Ser Lys Thr Arg Ala Ala
                660                 665                 670
Leu Gly Val
```

<210> SEQ ID NO 3
<211> LENGTH: 1795
<212> TYPE: DNA
<213> ORGANISM: Artificial Sequence
<220> FEATURE:
<223> OTHER INFORMATION: chemically synthesized
<220> FEATURE:
<221> NAME/KEY: CDS
<222> LOCATION: (1)..(1782)

<400> SEQUENCE: 3

```
atg gct aaa ggt acc ttg cat aga aat gaa tat ggt att gct tct att     48
Met Ala Lys Gly Thr Leu His Arg Asn Glu Tyr Gly Ile Ala Ser Ile
1               5                   10                  15 ttg gat tct tat caa tgt act gct gaa att tct ttg gct gat ttg gct     96
Leu Asp Ser Tyr Gln Cys Thr Ala Glu Ile Ser Leu Ala Asp Leu Ala
                20                  25                  30 act att ttt ttt gct caa ttt gtt caa gaa gct act tat aaa gaa gtt    144
Thr Ile Phe Phe Ala Gln Phe Val Gln Glu Ala Thr Tyr Lys Glu Val
            35                  40                  45 tct aaa atg gtt aaa gat gct ttg act gct att gaa aaa cca act ggt    192
Ser Lys Met Val Lys Asp Ala Leu Thr Ala Ile Glu Lys Pro Thr Gly
        50                  55                  60 gat gaa caa tct tct ggt tgt ttg gaa aat caa ttg cca gct ttt ttg    240
Asp Glu Gln Ser Ser Gly Cys Leu Glu Asn Gln Leu Pro Ala Phe Leu
65                  70                  75                  80 gaa gaa ttg tgt cat gaa aaa gaa att ttg gaa aaa tat ggt cat tct    288
Glu Glu Leu Cys His Glu Lys Glu Ile Leu Glu Lys Tyr Gly His Ser
                85                  90                  95 gat tgt tgt tct caa tct gaa gaa ggt aga cat aat tgt ttt ttg gct    336
Asp Cys Cys Ser Gln Ser Glu Glu Gly Arg His Asn Cys Phe Leu Ala
                100                 105                 110 cat aaa aaa cca act cca gct tct att cca ttg ttt caa gtt cca gaa    384
His Lys Lys Pro Thr Pro Ala Ser Ile Pro Leu Phe Gln Val Pro Glu
            115                 120                 125 cca gtt aca tct tgt gaa gca tat gaa gaa gat aga gaa act ttt atg    432
Pro Val Thr Ser Cys Glu Ala Tyr Glu Glu Asp Arg Glu Thr Phe Met
        130                 135                 140 aat aaa ttt att tat gaa att gct aga aga cat cca ttt ttg tat gct    480
Asn Lys Phe Ile Tyr Glu Ile Ala Arg Arg His Pro Phe Leu Tyr Ala
145                 150                 155                 160 cca act att ttg ttg tgg gct gct aga tat gat aaa att att cca tct    528
Pro Thr Ile Leu Leu Trp Ala Ala Arg Tyr Asp Lys Ile Ile Pro Ser
                165                 170                 175 tgt tgt aaa gct gaa aat gct gtt gaa tgt ttt caa act aaa gct gct    576
Cys Cys Lys Ala Glu Asn Ala Val Glu Cys Phe Gln Thr Lys Ala Ala
                180                 185                 190 act gtt act aaa gaa ttg aga gaa tct tct ttg ttg aat caa cac gca    624
Thr Val Thr Lys Glu Leu Arg Glu Ser Ser Leu Leu Asn Gln His Ala
            195                 200                 205 tgc gct gtt atg aaa aat ttt ggt act aga act ttt caa gct att act    672
Cys Ala Val Met Lys Asn Phe Gly Thr Arg Thr Phe Gln Ala Ile Thr
        210                 215                 220 gtt act aaa ttg tct caa aaa ttt act aaa gtt aat ttt act gaa att    720
Val Thr Lys Leu Ser Gln Lys Phe Thr Lys Val Asn Phe Thr Glu Ile
225                 230                 235                 240 caa aaa ttg gtt ttg gat gtt gct cat gtt cat gaa cat tgt tgt aga    768
Gln Lys Leu Val Leu Asp Val Ala His Val His Glu His Cys Cys Arg
                245                 250                 255 ggt gat gtt ttg gat tgt ttg caa gat ggt gaa aaa att atg tct tat    816
```

```
Gly Asp Val Leu Asp Cys Leu Gln Asp Gly Glu Lys Ile Met Ser Tyr
            260                 265                 270 att tgt tct caa caa gat act ttg tct aat aaa att act gaa tgt tgt    864
Ile Cys Ser Gln Gln Asp Thr Leu Ser Asn Lys Ile Thr Glu Cys Cys
        275                 280                 285 aaa ttg act act ttg gaa aga ggt caa tgc att att cat gct gaa aat    912
Lys Leu Thr Thr Leu Glu Arg Gly Gln Cys Ile Ile His Ala Glu Asn
            290                 295                 300 gat gaa aaa cca gaa ggt ttg tct cca aat ttg aat aga ttt ttg ggt    960
Asp Glu Lys Pro Glu Gly Leu Ser Pro Asn Leu Asn Arg Phe Leu Gly
305                 310                 315                 320 gat aga gat ttt aat caa ttt tct tct ggt gaa aaa aat att ttt ttg   1008
Asp Arg Asp Phe Asn Gln Phe Ser Ser Gly Glu Lys Asn Ile Phe Leu
                325                 330                 335 gct tct ttt gtt cat gaa tat tct aga aga cat cca caa tta gct gtt   1056
Ala Ser Phe Val His Glu Tyr Ser Arg Arg His Pro Gln Leu Ala Val
            340                 345                 350 tct gtt att ttg aga gtt gct aaa ggt tat caa gaa ttg ttg gaa aaa   1104
Ser Val Ile Leu Arg Val Ala Lys Gly Tyr Gln Glu Leu Leu Glu Lys
        355                 360                 365 tgt ttt caa act gaa aat cca ttg gaa tgt caa gat aaa ggt gaa gaa   1152
Cys Phe Gln Thr Glu Asn Pro Leu Glu Cys Gln Asp Lys Gly Glu Glu
370                 375                 380 gaa ttg caa aaa tat att caa gaa tct caa gca ttg gct aaa aga tct   1200
Glu Leu Gln Lys Tyr Ile Gln Glu Ser Gln Ala Leu Ala Lys Arg Ser
385                 390                 395                 400 tgt ggt ttg ttt caa aaa ttg ggt gaa tat tat ttg caa aat gct ttt   1248
Cys Gly Leu Phe Gln Lys Leu Gly Glu Tyr Tyr Leu Gln Asn Ala Phe
            405                 410                 415 ttg gtt gct tat act aaa aaa gct cca caa tta act tct tct gaa ttg   1296
Leu Val Ala Tyr Thr Lys Lys Ala Pro Gln Leu Thr Ser Ser Glu Leu
        420                 425                 430 atg gct att act aga aaa atg gct gct act gct gct act tgt tgt caa   1344
Met Ala Ile Thr Arg Lys Met Ala Ala Thr Ala Ala Thr Cys Cys Gln
                435                 440                 445 tta tct gaa gat aaa ttg ttg gct tgt ggt gaa ggt gct gct gat atc   1392
Leu Ser Glu Asp Lys Leu Leu Ala Cys Gly Glu Gly Ala Ala Asp Ile
            450                 455                 460 att att ggt cat ttg tgt att aga cat gaa atg act cca gtt aat cca   1440
Ile Ile Gly His Leu Cys Ile Arg His Glu Met Thr Pro Val Asn Pro
465                 470                 475                 480 ggt gtt ggt caa tgt tgt act tct tct tat gct aat aga aga cca tgt   1488
Gly Val Gly Gln Cys Cys Thr Ser Ser Tyr Ala Asn Arg Arg Pro Cys
                485                 490                 495 ttt tct tct ttg gtt gtt gat gaa act tat gtt cca cca gct ttt tct   1536
Phe Ser Ser Leu Val Val Asp Glu Thr Tyr Val Pro Pro Ala Phe Ser
            500                 505                 510 gat gat aaa ttt att ttt cat aaa gat ttg tgt caa gct caa ggt gtt   1584
Asp Asp Lys Phe Ile Phe His Lys Asp Leu Cys Gln Ala Gln Gly Val
        515                 520                 525 gct ttg caa act atg aaa caa gaa ttc ttg att aat ttg gtt aaa caa   1632
Ala Leu Gln Thr Met Lys Gln Glu Phe Leu Ile Asn Leu Val Lys Gln
530                 535                 540 aaa cca caa att act gaa gaa caa tta gaa gct gtt att gct gat ttt   1680
Lys Pro Gln Ile Thr Glu Glu Gln Leu Glu Ala Val Ile Ala Asp Phe
545                 550                 555                 560 tct ggt ttg ttg gaa aaa tgt tgt caa ggt caa gaa caa gaa gtt tgt   1728
Ser Gly Leu Leu Glu Lys Cys Cys Gln Gly Gln Glu Gln Glu Val Cys
                565                 570                 575 ttt gct gaa gaa ggt caa aaa ttg att tct aaa act aga gct gct ttg   1776
```

Phe Ala Glu Glu Gly Gln Lys Leu Ile Ser Lys Thr Arg Ala Ala Leu
            580                 585                 590 ggt gtt taactcgaga tat                                                      1795
Gly Val <210> SEQ ID NO 4
<211> LENGTH: 594
<212> TYPE: PRT
<213> ORGANISM: Artificial Sequence
<220> FEATURE:
<223> OTHER INFORMATION: Synthetic Construct

<400> SEQUENCE: 4

Met Ala Lys Gly Thr Leu His Arg Asn Glu Tyr Gly Ile Ala Ser Ile
1               5                   10                  15

Leu Asp Ser Tyr Gln Cys Thr Ala Glu Ile Ser Leu Ala Asp Leu Ala
            20                  25                  30

Thr Ile Phe Phe Ala Gln Phe Val Gln Glu Ala Thr Tyr Lys Glu Val
        35                  40                  45

Ser Lys Met Val Lys Asp Ala Leu Thr Ala Ile Glu Lys Pro Thr Gly
50                  55                  60

Asp Glu Gln Ser Ser Gly Cys Leu Glu Asn Gln Leu Pro Ala Phe Leu
65                  70                  75                  80

Glu Glu Leu Cys His Glu Lys Glu Ile Leu Glu Lys Tyr Gly His Ser
                85                  90                  95

Asp Cys Cys Ser Gln Ser Glu Glu Gly Arg His Asn Cys Phe Leu Ala
            100                 105                 110

His Lys Lys Pro Thr Pro Ala Ser Ile Pro Leu Phe Gln Val Pro Glu
        115                 120                 125

Pro Val Thr Ser Cys Glu Ala Tyr Glu Glu Asp Arg Glu Thr Phe Met
    130                 135                 140

Asn Lys Phe Ile Tyr Glu Ile Ala Arg Arg His Pro Phe Leu Tyr Ala
145                 150                 155                 160

Pro Thr Ile Leu Leu Trp Ala Ala Arg Tyr Asp Lys Ile Ile Pro Ser
                165                 170                 175

Cys Cys Lys Ala Glu Asn Ala Val Glu Cys Phe Gln Thr Lys Ala Ala
            180                 185                 190

Thr Val Thr Lys Glu Leu Arg Glu Ser Ser Leu Leu Asn Gln His Ala
        195                 200                 205

Cys Ala Val Met Lys Asn Phe Gly Thr Arg Thr Phe Gln Ala Ile Thr
    210                 215                 220

Val Thr Lys Leu Ser Gln Lys Phe Thr Lys Val Asn Phe Thr Glu Ile
225                 230                 235                 240

Gln Lys Leu Val Leu Asp Val Ala His Val His Glu His Cys Cys Arg
                245                 250                 255

Gly Asp Val Leu Asp Cys Leu Gln Asp Gly Glu Lys Ile Met Ser Tyr
            260                 265                 270

Ile Cys Ser Gln Gln Asp Thr Leu Ser Asn Lys Ile Thr Glu Cys Cys
        275                 280                 285

Lys Leu Thr Thr Leu Glu Arg Gly Gln Cys Ile Ile His Ala Glu Asn
    290                 295                 300

Asp Glu Lys Pro Glu Gly Leu Ser Pro Asn Leu Asn Arg Phe Leu Gly
305                 310                 315                 320

Asp Arg Asp Phe Asn Gln Phe Ser Ser Gly Glu Lys Asn Ile Phe Leu
                325                 330                 335

Ala Ser Phe Val His Glu Tyr Ser Arg Arg His Pro Gln Leu Ala Val

```
                340                 345                 350
Ser Val Ile Leu Arg Val Ala Lys Gly Tyr Gln Glu Leu Leu Glu Lys
        355                 360                 365
Cys Phe Gln Thr Glu Asn Pro Leu Glu Cys Gln Asp Lys Gly Glu Glu
    370                 375                 380
Glu Leu Gln Lys Tyr Ile Gln Glu Ser Gln Ala Leu Ala Lys Arg Ser
385                 390                 395                 400
Cys Gly Leu Phe Gln Lys Leu Gly Glu Tyr Tyr Leu Gln Asn Ala Phe
                405                 410                 415
Leu Val Ala Tyr Thr Lys Lys Ala Pro Gln Leu Thr Ser Ser Glu Leu
            420                 425                 430
Met Ala Ile Thr Arg Lys Met Ala Ala Thr Ala Ala Thr Cys Cys Gln
        435                 440                 445
Leu Ser Glu Asp Lys Leu Leu Ala Cys Gly Glu Gly Ala Ala Asp Ile
    450                 455                 460
Ile Ile Gly His Leu Cys Ile Arg His Glu Met Thr Pro Val Asn Pro
465                 470                 475                 480
Gly Val Gly Gln Cys Cys Thr Ser Ser Tyr Ala Asn Arg Arg Pro Cys
                485                 490                 495
Phe Ser Ser Leu Val Val Asp Glu Thr Tyr Val Pro Pro Ala Phe Ser
            500                 505                 510
Asp Asp Lys Phe Ile Phe His Lys Asp Leu Cys Gln Ala Gln Gly Val
        515                 520                 525
Ala Leu Gln Thr Met Lys Gln Glu Phe Leu Ile Asn Leu Val Lys Gln
    530                 535                 540
Lys Pro Gln Ile Thr Glu Glu Gln Leu Glu Ala Val Ile Ala Asp Phe
545                 550                 555                 560
Ser Gly Leu Leu Glu Lys Cys Cys Gln Gly Gln Glu Gln Glu Val Cys
                565                 570                 575
Phe Ala Glu Glu Gly Gln Lys Leu Ile Ser Lys Thr Arg Ala Ala Leu
            580                 585                 590
Gly Val

<210> SEQ ID NO 5
<211> LENGTH: 23
<212> TYPE: DNA
<213> ORGANISM: Artificial Sequence
<220> FEATURE:
<223> OTHER INFORMATION: primer

<400> SEQUENCE: 5
gaagtaattt aaactcccaa agc                                        23

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
cttcaatcga tatgacactg catagaaatg                                 30

<210> SEQ ID NO 7
<211> LENGTH: 26
<212> TYPE: DNA
<213> ORGANISM: Artificial Sequence
<220> FEATURE:
<223> OTHER INFORMATION: primer
```

```
<400> SEQUENCE: 7
cttccaagct taaactccca aagcag                                              26

<210> SEQ ID NO 8
<211> LENGTH: 26
<212> TYPE: DNA
<213> ORGANISM: Artificial Sequence
<220> FEATURE:
<223> OTHER INFORMATION: primer

<400> SEQUENCE: 8
caaccctcga gttaaactcc caaagc                                              26

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
ccaacccatg gctaagagaa cactgcatag aaatg                                    35
```